US006710088B2

(12) United States Patent
Moe et al.

(10) Patent No.: US 6,710,088 B2
(45) Date of Patent: *Mar. 23, 2004

(54) INORGANIC ION RECEPTOR-ACTIVE COMPOUNDS

(75) Inventors: Scott T. Moe, Salt Lake City, UT (US); Bradford C. Van Wagenen, Salt Lake City, UT (US); Eric G. DelMar, Salt Lake City, UT (US); Richard Trovato, Salt Lake City, UT (US); Manuel F. Balandrin, Sandy, UT (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/060,959

(22) Filed: Jan. 29, 2002

(65) Prior Publication Data

US 2003/0008876 A1 Jan. 9, 2003

Related U.S. Application Data

(60) Continuation of application No. 09/415,179, filed on Oct. 6, 1999, now Pat. No. 6,342,532, which is a division of application No. 08/846,721, filed on Apr. 30, 1997, now Pat. No. 5,981,599.
(60) Provisional application No. 60/016,673, filed on May 1, 1996.

(51) Int. Cl.[7] .................................. A61K 31/135
(52) U.S. Cl. ........................ 514/654; 514/655
(58) Field of Search .................. 564/374, 378, 564/381, 384, 387, 389, 392; 514/654, 655

(56) References Cited

U.S. PATENT DOCUMENTS

| | | | |
|---|---|---|---|
| 2,276,618 A | 3/1942 | Kulz ..................... 260/520.8 |
| 2,930,731 A | 3/1960 | Heinzelmann et al. ...... 514/555 |
| 2,949,359 A | 8/1960 | Blout et al. .................. 430/441 |
| 3,202,711 A | 8/1965 | Fruhstorfer et al. ........ 260/570 |
| 3,262,977 A | 7/1966 | Harsanyi et al. ............. 564/316 |
| 3,493,662 A | 2/1970 | Duerr et al. .................. 514/654 |
| 3,536,712 A | 10/1970 | Keck et al. .................. 200/253 |
| 3,689,524 A | 9/1972 | Jack et al. ............... 260/471 A |
| 3,842,067 A | 10/1974 | Sarantakis .................. 530/311 |
| 3,862,925 A | 1/1975 | Sarantakis .................. 530/311 |
| 3,972,859 A | 8/1976 | Fujino et al. ................ 530/313 |
| 4,000,197 A | 12/1976 | Barfknecht et al. ...... 260/870.8 |
| 4,014,937 A | 3/1977 | Richardson .......... 260/570.8 R |
| 4,098,890 A | 7/1978 | Molloy .................... 424/248.4 |
| 4,105,602 A | 8/1978 | Colescott et al. ........... 514/620 |
| 4,242,355 A | 12/1980 | Nedelec et al. ............. 424/275 |
| 4,289,787 A | 9/1981 | Molloy et al. ............... 424/329 |
| 4,360,511 A | 11/1982 | Baldwin et al. .............. 424/1.5 |
| 4,391,826 A | 7/1983 | Mills et al. .................. 424/324 |
| 4,487,965 A | 12/1984 | Himmele et al. ............ 564/454 |
| 4,587,253 A | 5/1986 | Halczenko et al. ......... 514/289 |
| 4,591,605 A | 5/1986 | Ray et al. .................... 514/579 |
| 4,608,391 A | 8/1986 | Ginos et al. ................. 514/654 |
| 4,609,494 A | 9/1986 | Baldwin et al. ............. 544/250 |
| 4,647,446 A | 3/1987 | Sargent et al. ................ 424/1.1 |
| 4,661,635 A | 4/1987 | Carson ....................... 564/374 |
| 4,675,321 A | 6/1987 | Baldwin et al. ............. 514/275 |
| 4,677,101 A | 6/1987 | Claremon et al. .......... 514/215 |
| 4,769,483 A | 9/1988 | Lombardi et al. ............ 560/19 |
| 4,797,411 A | 1/1989 | Crugnola et al. ........... 514/357 |
| 4,808,718 A | 2/1989 | Hartman et al. .............. 546/14 |
| 4,839,369 A | 6/1989 | Youssefyeh et al. ........ 514/314 |
| 4,916,145 A | 4/1990 | Tilley et al. ................. 514/357 |
| 4,925,664 A | 5/1990 | Jackson et al. ............. 424/537 |
| 4,925,873 A | 5/1990 | Friedhoff et al. ........... 514/469 |
| 4,967,003 A | 10/1990 | Rentzea et al. ............. 564/381 |
| 4,988,730 A | 1/1991 | Korbonits et al. .......... 514/466 |
| 5,001,251 A | 3/1991 | MacManus et al. ........ 558/255 |
| 5,011,834 A | 4/1991 | Weber et al. ................ 514/212 |
| 5,021,599 A | 6/1991 | Beer et al. ................... 536/142 |
| 5,030,576 A | 7/1991 | Dull et al. .................. 435/63.7 |
| 5,034,514 A | 7/1991 | Nitecki et al. ............ 530/351.1 |
| 5,053,337 A | 10/1991 | Weinshank et al. ...... 435/240.2 |
| 5,064,657 A | 11/1991 | Jackson et al. ............. 424/537 |
| 5,073,648 A | 12/1991 | Hagashita et al. .......... 564/374 |
| 5,075,338 A | 12/1991 | Knoll et al. ................. 514/654 |
| 5,082,837 A | 1/1992 | Palfreyman ................. 514/183 |
| 5,334,628 A | 8/1994 | Maeda et al. ............... 514/311 |
| 5,403,861 A | 4/1995 | Goldin et al. ............... 514/634 |
| 5,504,253 A | 4/1996 | VanWagenen et al. ...... 564/374 |
| 5,648,541 A | 7/1997 | VanWagenen et al. ...... 564/375 |
| 5,763,569 A | 6/1998 | Brown et al. ............... 530/324 |
| 5,981,599 A * | 11/1999 | Moe et al. ................... 514/654 |
| 6,001,884 A | 12/1999 | Nemeth et al. ............. 514/699 |
| 6,342,532 B1 * | 1/2002 | Moe et al. ................... 514/648 |

FOREIGN PATENT DOCUMENTS

| BE | 62 1300 | 12/1962 |
| CN | 1 065 857 | 11/1992 |

(List continued on next page.)

OTHER PUBLICATIONS

Arendsen, et al., *Chemical Abstracts*, vol. 129:343334 (1998).
Airapetyan, et al., *Chemical Abstracts*, vol. 104:28398 (1986).
Berney, *Chemical Abstracts*, vol. 95:168865 (1981).
Euerby, et al., *Chemical Abstracts*, vol. 107:175853 (1987).
Gao, et al., *Chemical Abstracts*, vol. 123:338595 (1995).
Grassberger, et al., *Chemical Abstracts*, vol. 104:129795 (1986).
Harsany, et al., *Chemical Abstracts*, vol. 85:20818 (1976).
Hashimoto, et al., *Chemical Abstracts*, vol. 124:116722 (1995).

(List continued on next page.)

*Primary Examiner*—Richard L. Raymond
(74) *Attorney, Agent, or Firm*—Richard J. Warburg; Foley & Lardner

(57) ABSTRACT

The present invention features compounds able to modulate one or more activities of an inorganic ion receptor and methods for treating diseases or disorders using such compounds. Preferred compounds can mimic or block the effect of extracellular calcium on a cell surface calcium receptor.

26 Claims, 6 Drawing Sheets

FOREIGN PATENT DOCUMENTS

| | | |
|---|---|---|
| CZ | 21 7009 | 7/1984 |
| DE | 1 231 690 | 1/1967 |
| DE | 2 541 184 | 4/1976 |
| DE | 2 825 961 | 1/1980 |
| DE | 3541181 A | 5/1987 |
| EP | 0 009 702 | 9/1979 |
| EP | 0 005 848 | 12/1979 |
| EP | 0 007 204 | 1/1980 |
| EP | 0 015 505 | 9/1980 |
| EP | 0 023 385 | 2/1981 |
| EP | 0 044 158 | 1/1982 |
| EP | 0 101 069 | 8/1983 |
| EP | 0 092 787 | 11/1983 |
| EP | 0 200 101 | 12/1986 |
| EP | 0 253 327 | 1/1988 |
| EP | 0 270 376 | 7/1988 |
| EP | 0 289 287 | 11/1988 |
| EP | 0 309 100 | 3/1989 |
| EP | 0 395 357 | 10/1990 |
| EP | 0 408 284 | 1/1991 |
| EP | 0 224 163 | 10/1991 |
| EP | 0 455 510 | 11/1991 |
| EP | 0 508 307 | 10/1992 |
| GB | 1 079 091 | 8/1967 |
| GB | 1 109 924 | 4/1968 |
| GB | 1 448 437 | 2/1974 |
| GB | 1 464 209 | 2/1977 |
| GB | 2 113 089 | 11/1982 |
| GB | 2 213 818 | 8/1989 |
| JP | 5 390 272 | 8/1978 |
| JP | 5 950 358 | 3/1984 |
| JP | 2 200 658 | 8/1990 |
| WO | 82/04052 | 11/1982 |
| WO | 89/06135 | 7/1989 |
| WO | 89/09834 | 10/1989 |
| WO | 91/00853 | 1/1991 |
| WO | 91/09594 | 7/1991 |
| WO | 92/07829 | 5/1992 |
| WO | 92/14709 | 9/1992 |
| WO | 93/04373 | 4/1993 |
| WO | 93/10073 | 5/1993 |
| WO | 93/13052 | 7/1993 |
| WO | 93/15044 | 8/1993 |
| WO | 94/18959 | 9/1994 |
| WO | 95/11221 | 4/1995 |
| WO | 0 443 606 | 5/1995 |
| WO | 95/18134 | 7/1995 |
| WO | 95/21815 | 8/1995 |
| WO | 96/12697 | 5/1996 |

OTHER PUBLICATIONS

Hayashi, et al., *Chemical Abstracts*, vol. 111:78343 (1989).

Kametani, et al., *Chemical Abstracts*, vol. 72:54913 (1970).

Palacios, et al., *Chemical Abstracts*, vol. 125:195818 (1996).

Schatz et al., *Chemical Abstracts*, vol. 104:218539 (1986).

Stuetz et al., *Chemical Abstracts*, vol. 104:68547 (1986).

Stuetz et al., *Chemical Abstracts*, vol. 104:148578 (1986).

Stuetz, et al., "Synthesis and Structure Relationships of Naftifine–Related Allylamine Antimyotics," *Journal of Medicinal Chemistry*, 29(1):122–125 (1986).

Togni, et al., *Chemical Abstracts*, vol. 124:201696 (1996).

Database Crossfire, Beilstein Informationssysteme GmbH, Frankfurt DE, XP002037081, *J. Chem. Res. Miniprint*, 10:3529–3249 (1981).

Database Crossfire, Beilstein Informationssysteme GmbH, Frankfurt DE, XP002037082, *Arzneim. Forsch*, 17:1145–1149 (1967).

Database Crossfire, Beilstein Informationssysteme GmbH, Frankfurt DE, XP002037083, *J. Chem.Soc. Chem. Commun.* 1421–1422 (1995).

Database Crossfire, Beilstein Informationssysteme GmbH, Frankfurt DE, XP002037084, Chem. *Pharm. Bull.* 31:3471–3485 (1983).

Database Crossfire, Beilstein Informationssysteme GmbH, Frankfurt DE, XP002037085, *Arch. Pharm* 326:341–350 (1993).

Anderson and Santi, "Phenylalanyl Transfer Ribonucleic Acid Synthetase from *Escherichia coli* B. Potent Inhibition by Analogues of N–Benzyl–2–phenylethylamine," *J. Med. Chem.* 19:1270–1275 (1976).

Arjona et al., "Sterochemistry of the reduction of the imino group. IV. Sterochemistry of the reduction of N–(1–phenylethyl)–1–alkyl–1–arylmethanimines," *An. Quim. Ser. C* 81(1):23–29 (1985).

Barney et al., "A Convenient Synthesis of Hindered Amines and α–Trifluoromethylamines from Ketones," *Tetrahedron Letters* 31:5547–5550 (1990).

Batra and Alenfall, "Effects of Diverse Categories of Drugs on Human Colon Tumour Cell Proliferation," *Anticancer Research* 11:1221–1224 (1991).

Becalski et al., "Catalytic asymmetric hydrogenation of imines. Use of rhodium(I)/phosphine comploexes and characterization of rhodium(I)/imine complexes," *Chemical Abstracts* 116:558 at Abstract No. 14742U (1992).

Bertz et al., "Asymmetric Induction with Amidocuprates," *J. Org. Chem.* 51:4953–4959 (1986).

Boyd et al., "Dynamic Sterochemistry of Imines and Derivatives. Part 18. Photosynthesis and Photoracemization of Optically Active Oxaziridines," *J. Chem. Soc. Perkin Trans. I* 4:849–855 (1985).

Bringmann et al., "Enantiomerically Pure N–Boc Protected β–Keto–γ–Amino Acid Esters from Simple Keto Precursors: A Novel, Stereocontrolled Approach to Statine Derivatives with Any Desired Configuration," *SYNLET Letters* pp. 253–255 (1990).

Bringmann et al., "The Enantioselective Synthesis of Optically Active, Benzene Nucleus–Substituted 1–Phenylethylamines from the Corresponding Acetophenones," *Leibigs Ann.Chem.* 5:795–805 (1990).

Brown et al, "Cloning and characterization of an extracellular $Ca^{2+}$ sensing receptor from bovine parathryoid," *Nature* 366:575–580 (1993).

Brown et al., "A Comparison of the Effects of Divalent and Trivalent Cations on Parathyroid Hormone Release, 3', 5'–Cyclic–Adenosine Monophosphate Accumulation, and the Levels of Inositol Phosphates in Bovine Parathyroid Cells," *Endocrinology* 127:1064–1071 (1990).

Brown et al., "High Extracellular $Ca^{2+}$ and $Mg^{2+}$ Stimulate Accumulation of Inositol Phosphates in Bovine Parathyroid Cells," *FEBS Letters* 218:113–118 (1987).

Brown et al., "Neomycin Mimics the Effects of High Extracellular Calcium Concentrations on Parathyroid Function in Dispersed Bovine Parathyroid Cells," *Endocrinology* 128:3047–3054 (1991).

Brown et al., "Polyarginine, Polylysine, and Protamine Mimic the Effects of High Extracellular Calcium Concentrations on Dispersed Bovine Parathyroid Cells," *Journal of Bone and Mineral Research* 6:1217–1225 (1991).

Brown et al., Chemical Abstracts, vol. 128 abstract 30379 (1997).
Brown, "Extracellular $Ca^{2+}$ Sensing, Regulation of Parathyroid Cell Function and Role of $Ca^{2+}$ and Other Ions as Extracellular (First) Messengers," *Physiological Reviews* 71:371–411 (1991).
Burke et al., "Mono–1,3–benzoxazines from hydroquinone," *J. Org. Chem.* 28:1098–110 (1963).
Capuano et al., "Characterization of the Human Calcium Receptor Gene," *Journal of Bone and Mineral Research* 9(1):S145 at abstract No. 98 (1994).
*Chemical Abstracts Formula Index*, vol. 110 p. 1793F (1989).
*Chemical Abstracts Formula Index*, vol. 110 p. 537F (1989).
Chen and Brown, "The Diltiazem Analog TA–3090 Mimics the Actions of High Extracellular $Ca^{2+}$ on Parathyroid Function in Dispersed Bovine Parathyroid Cells," *Journal of Bone and Mineral Research* 5:581–587 (1990).
Chen et al., "Injection of Bovine Parathyroid Poly(A)$^{+RNA}$ into Xenopus Oocytes Confers Sensitivity to High Extracellular Calcium," *Journal of Bone and Mineral Research* 9:293–300 (1994).
Clifton et al., "Arylethanolamines derived from salicylamide with alpha– and beta–adrenoceptor blocking activities. Preparation of labetalol, its enantiomers and related salicylamides," *J. Med. Chem.* 25:670–679 (1982).
Danks, "Reaction of Hydride Transfer Reducing Agents with (1–Heterodiene) Tricarbonyliron(0) Complexes and the Synthesis of Saturated Amines and Alcohols," *Tetrahedron Letters* 35:4177–4178 (1994).
Davies and Ichihara, "Asymmetric Synthesis of R–β–Amino Butanoic Acid and S–β–Tyrosine: Homochiral Lithium Amide Equivalents for Michael Additions to α,β–Unsaturated Esters," *Tetrahedron: Asymmetry* 2:183–186 (1991).
De Feo et al., "Natriuretic Peptide Receptors Regulate Endothelin Synthesis and Release From Parathyroid Cells," *Proc. Natl. Acad. Sci. USA* 88:6496–6500 (1991).
Fox et al., "A First Generation Calcimimetic Compound (NPS R–568) That Acts on the Parathyroid Cell Calcium Receptor: A Novel Therapeutic Approach for Hyperparathyroidism," *Journal of Bone and Mineral Research* 8(1):S181 at abstract No. 260 (1993).
Fox et al., "NPS R–568 Acts on Calcium Receptors to Inhibit Parathyroid Hormone and Stimulate Calcitonin Secretion: A Novel Therapeutic Approach for Hyperparathyroidisum," *J. American Society of Nephrology* 4:719 at abstract No. 120P (1993).
Fox et al., "NPS R–568 Inhibits Parathyroid Hormone Secretion and Stimulates Calcitonin Secretion in Hyperparathyroid Rats with Chronic Renal Failure," *J. American Society of Nephrology* 4:719 at abstract No. 69P (1993).
Fox et al., "Parathyroid Gland Calcium Receptor Gene Expression is Unaffected by Chronic Renal Failure or Low Dietary Calcium in Rats," *J. Am. Soc. Nephrology* 5:879 at abstract No. 90P (1994).
Fox et al., "Physiologically Relevant PTH Levels are Anabolic on Bone in Ovariectomized Rats," *Bone* 16(Supplement): 194S at abstract No. 434 (1995).
Fox et al., "Prevention of Hypocalcemia Prolongs the Plasma Parathyroid Hormone and Calcitonin Responses to the Calcimimetic Compound NPS R–568 in Rats," *Journal of Bone and Mineral Research* 9(1):S409 at abstract No. C396 (1994).

Fraser et al., "Substitution α to the Nitrogen in Dibenzylamine via Carbanion Intermediates," *Can J. Chem.* 51:1109–1115 (1973).
Freifelder, "Selective Hydrogenolysis. Dehalogenation in the Presence of N–Benzyl Linkage," *J. Org. Chem.* 31(11):3875–3877 (1966).
Fuji et al., "Endothelin as an Autocrine Factor in the Regulation of Parathyroid Cells," *Proc. Natl. Acad. Sci. USA* 88:4235–4239 (1991).
Fuleihan et al., "Effects on the Lectin Concanavalin–A on Calcium–Regulated Adenosine 3',5'–Monophosphate Accumulation in Bovine Parathyroid Cells," *Endocrinology* 126:1996–2002 (1990).
Fuleihan et al., "Effects of the Lectin Concanavalin–A on the Regulation of Second Messengers and Parathyroid Hormone Release by Extracellular $Ca^{2+}$ in Bovine Parathyroid Cells," *Endocrinology* 128:2931–2936 (1991).
Garrett et al., "Calcitonin–Secreting Cells of the Thyroid Express an Extracellular Calcium Receptor Gene," *Endocrinology* 136(11):5202–5211 (1995).
Garrett et al., "Cloning and Expression of a G–Protein–Coupled Calcium Receptor From a Human Parathyroid Adenoma," *Journal of Bone and Mineral Research* 8 (Supplement 1):S148 at abstract No. 125 (1993).
Garrett et al., "Expression of the Parathyroid Calcium Receptor Gene in C–Cells," *Journal of Bone and Mineral Research* 9(1):S409 at abstract No. C398 (1994).
Giovambattista et al., "Investigaciones Recientes," *Ciencia e invest.* (Buenos Aires) 14, 34–35 (1968).
Gracheva et al., "Stereodirection of Ketimine Reduction Reactions," *Zhural Organicheskoi Khimii* 9(6):1235–1239 (1973).
Gracheva et al., "The Stereoselectivity of the Reactions of Schiff Bases with Organomagnesium Compounds," *Zhural Organicheskoi Khimii* 10(3):557–561 (1974).
Grethe et al., "Syntheses in the Isoquinoline Series. Synthesis of 2,3–Dihydro–4(1H)–isoquinolones," *J. Org. Chem.* 33(2):491–494 (1968).
Hamana et al., Chemical Abstracts, vol. 117 abstract 8523 (1992).
Hammerland et al., "Mechanism of Action of the Calcimimetic Compounds NPS R–467 and NPS R–568 in Xenopus Oocytes Expressing a Bovine Parathyroid Cell Calcium Receptor," *Journal of Bone and Mineral Research* 8(Supplement 1):S133 at abstract No. 65 (1993).
Harootunian et al., "Effects of Calcitonin and Extracellular Calcium on Cytosolic Levels of Cyclic AMP and $Ca^{2+}$ in Rabbit Osteoclasts," *Journal of Bone and Mineral Research* 9(1):S246 at abstract No. B66 (1994).
Hashimoto et al., "Highly Diastereoselective Addition of Organometallic Reagents to Chiral Imines Derived from 1–(2–Methoxyphenyl)ethylamine," *Synlett Letters* pp. 961–962 (1995).
Hawkins et al., "The Effects of High Extracellular $Ca^{2+}$ and $Mg^{2+}$ Concentrations on the Levels of Inositol 1,3,4,5–Tetrakisphosphate in Bovine Parathyroid Cells," *Endocrinology* 124:838–844 (1989).
Heath et al., "Inhibition of Human Parathyroid Hormone Secretion In Vivo by NPS R–568, a Calcimimetic Drug that Targets the Parathyroid Cell–Surface Calcium Receptor," *Bone* 16(Supplement):85S at abstract No. 23 (1995).
Hiroi et al., "A Highly Efficient and Recyclable Chiral Director for Asymmetric Synthesis of Sulfoxides," *Chemistry Letters* pp. 1595–1598 (1980).

Hiroi et al., "Studies on Chiral Organo–Sulfur Compounds. I. Asymmetric Synthesis of Sulfoxides with Optically Active o–Aminoalkylphenol Derivatives," *Chem. Pharm. Bull.* 31:3471–3485 (1983).

Höltje and Maurhofer, "Conformational Analysis on Calcium Channel Active Diphenylalkylamines, Diphenylbutylpiperidines, Phenylalkylamines, and Perhexiline," *Quant. Struct.–Act. Relat.* 8:259–265 (1989).

Hu et al., "Lithium hydride elimination in the reactions of organolithium compounds with imines: synthesis of secondary amines with branched groups," *C.R. Acad. Sci. Paris Ser. C* 284(4):195–198 (1977).

Hung et al., "Coupling of the Porcine Calcitonin Receptor to Cytosolic $Ca^{2+}$ and cAMP Levels in Xenopus Oocytes," *Journal of Bone and Mineral Research* 9(1):S410 at abstract No. C400 (1994).

Hutton et al., "Organic Reagents for the Precipitation of Nitrate Ion. Part I. N–Substituted 1–naphthylmethylamines," *J. Chem. Soc.* (A) 11:1573–1579 (1966).

Ikegami et al., "Chemistry of Sodium Borohydride and Diborane. II. Reduction of Schiff Bases with Diborane in Tetrahydrofuran," *Chem. Pharm. Bull.* 14(12):1389–1399 (1966).

Jasys et al., "The Total Synthesis of Argiotoxins 636, 659 and 673," *Tetrahedron Letters* 29:6223–6226 (1988).

Joshi and Mehrotra, "Reductive Coupling In Substituted Imines with Aluminium–Amalgam in Moist Ether," *Nat. Acad. Sci. Letters (India)* 3:268–272 (1980).

Juaristi et al., "Use of N,N'–Dimethylpropyleneurea (DMPU) as Solvent in the Efficient Preparation of Enantiomerically Pure Secondary Amines," *Synthesis* pp. 1243–1246 (1993).

Kametani et al., "Studies on the Synthesis of Heterocyclic Compounds. Part 687. Asymmetric Synthesis of Salsolidine," *J. Chem. Soc. Perkin Trans. 1* pp. 579–581 (1977).

Kang et al., "Rhodium(I)–catalysed Asymmetric Hydrogenation of Imines," *J. Chem. Soc. Chem. Commun.* pp. 1466–1467 (1988).

Katritzky et al., "Convenient Preparations of Imines and Symmetrical Secondary Amines Possessing Primary or Secondary Alkyl Groups," *Synthesis* 9:703–708 (1991).

Katz et al., "Structure–Function Relationships for the Effects of Various Aminoglycoside Antibotics on Dispersed Bovine Parathyroid Cells," *Endocrinology* 131:903–910 (1992).

Kienzle et al., "1,5–Dihydroimidazoquinazolinones as blood platelet aggregation inhibitors," *Eur. J. Med. Chem.–Chem. Ther.* 17:547–556 (1982).

Kifor and Brown, "Relationship between Diacylglycerol Levels and Extracellular $Ca^{2+}$ in Dispersed Bovine Parathyroid Cells," *Endocrinology* 123:2723–2729 (1988).

Koenig et al., "Polyamines Mediate Androgenic Stimulation of Clacum Fluxes and Membrane Transport in Rat Heart Myocytes," *Circulation Research* 64:415–426 (1989).

Komeyoshi and Kudo, "Optically active amines and their manufacture, intermediates and uses," *Chemical Abstracts* 121:1060 at Abstract No. 230462Y (1994).

Komori et al., Chemical Abstracts, vol. 125 abstract 248173 (1996).

Kozlov et al., "Reductive animation of 1–acetylcyclohexene by nitriles," *Vestsi Akad. Navuk BSSR, Ser. Khim. Navuk* pp. 55–58 (1977).

Krohn et al., Chemical Abstracts, vol. 89 abstract 108861 (1978).

Langlois et al., "Asymmetric synthesis of amines by hydrosilylation of imines catalyzed by a chiral complex of rhodium," *Tetrahedron Lett.* 49:4865–4868 (1973).

Larsson et al., "Paradoxical effects of $K^+$ and D–600 on parathyroid hormone secretion and cytoplasmic $Ca^{2+}$ in normal bovine and pathological human parathyroid cells," *Biochimica et Biophysica Acta* 847:263–269 (1985).

Lavanchy, Archives Des Sciennces (Geneva) 11:252–255 (1958).

Lensink et al., "Diastereoselective hydrogenation and kinetic resolution of imines using rhodium/diphosphine catalyzed hydrogenation," *Tetrahedron: Asymmetry* 4:215–222 (1993).

Lensink and de Vries, "Improving Enantioselectivity by Using a Mono–Sulphonated Diphosphine as Ligand for Homogenous Imine Hydrogenation," *Tetrahedron:Assymetry* 3(2):235–238 (1992).

Leszkovszky et al., "The Pharmacology of Diphenylalkyl Derivatives," *Acta Physiologica Academiae Scientiarum Hungaricae Tomus* 29:283–297 (1966).

Levine, *Pharmacology: Drug Actions and Reactions*, Little Brown and Company, Inc. pp. 192–196 (1990).

Lopez–Barneo and Armstrong, "Depolarizing Response of Rat Parathyroid Cells to Divalent Cations," *J. Gen. Physiol.* 82:269–294 (1983).

Majewski and MacKinnon, "Enantioselective deprotonation of protected 4–hydroxycyclohexanones," *Can. J. Chem.* 72:1699–1704 (1994).

Majewski et al., "1,3,–Dioxan–5–ones: synthesis, deprotonation, and reactions of their lithium enolates," *Can. J. Chem.* 73:1616–1625 (1995).

Majewski et al., "Synthesis of Butenolides via Enantioselective Deprotonation of Protected 4–Hydroxycyclohexanone," *Tetrahedron Asymmetry* 6:1837–1840 (1995).

Mattson et al., "An Improved Method for Reductive Alkylation of Amines Using Titanium(IV) Isopropoxide and Sodium Cyanoborohydride," *J. Org. Chem.* 55:2552–2554 (1990).

Merck Index, 11th Edition, Monograph No. 2993, 2997, pp. 475 (1989).

Merck Index, 11th Edition, Monograph No. 3916, p. 623 (1989).

Merck Index, 11th Edition, Monograph No. 8699, pp. 420, 1379 (1989).

Merrifield, "Solid Phase Peptide Synthesis. I. The Synthesis of a Tetrapeptide," *J. Amer. Chem. Society* 85:2149–2154 (1963).

Mithal et al., "Highly Purified Sheep C–Cells Express an Extrececulluar $Ca^{2+}$ Receptor Similar to that Present in Parathyroid," *Journal of Bone and Mineral Research* 9(1):S282 at abstract No. B209 (1994).

Mori et al., "Formic Acid Reduction. XI. Reduction of Schiff Bases," *Chem. Pharm. Bull.* 19:1722–1727 (1971).

Muff et al., "Regulation of Hormone Secretion and Cytosolic $Ca^{2+}$ by Extracellular $Ca^{2+}$ in Parathyroid Cells and C–Cell: Role of Voltage–Sensitive $Ca^{2+}$ Channels," *Archives of Biochemistry and Biophysics* 265:128–135 (1988).

Nason et al., "Synthesis of Neurotoxic Nephlla Spider Venoms: NSTX–3 and JSTX–3," *Tetrahedron Letters* 30:2337–2340 (1989).

Nemeth and Carafoli, "The role of extracellular calcium in the regulation of intracellular calcium and cell function," *Cell Calcium* 11:319–321 (1990).

Nemeth and Scarpa, "Cystolic $Ca^{2+}$ and the regulation of secretion in parathyroid cells," *FEBS Letters* 203(1):15–19 (1986).

Nemeth and Scarpa, "Rapid Mobilization of Cellular $Ca^{2+}$ in Bovine Parathyroid Cells Evoked by Extracellular Divalent Cations –Evidence for a Cell Surface Calcium Receptor," *J. Biol. Chem.* 262(11):5188–5196 (1987).

Nemeth and Scarpa, "Receptor–Dependent Mobilization of Cellular $Ca^{2+}$ and the Regulation of Hormone Secretion in Parathyroid Cells," *Calcium Regulation and Bone Metabolism: Basic and Clinical Aspects* 9:167–171 (1987).

Nemeth and Scarpa, "Spermine Evokes the Rapid Mobilization of Cellular $Ca^{2+}$ in Parathyroid Cells," in *Calcium–Binding Proteins in Health and Disease*, Norman et al. editors, Academic Press, Inc., San Diego, pp. 33–35 (1987).

Nemeth et al., "Screening of compounds with potential action against calcium receptors and their use therapy of disorders of calcium metabolism," *Chemical Abstracts* 122(1):P1057y (1995).

Nemeth, "$Ca^{2+}$ Receptor–Dependent Regulation of Cellular Functions," *NIPS* 10:1–5 (1995) Check 1–15.

Nemeth, "Evidence for the Presence of a Novel $Ca^{2+}$–Binding Protein ($Ca^{2+}$ Receptor) on the Surface of Parathyroid Cells," *Calcium–Binding Proteins in Health and Disease*, Norman et al. editors, Academic Press, Inc., San Diego, pp. 36–38 (1987).

Nemeth, "Regulation of cystolic calcium by extracellular divalent cations in C–cells and parathyroid cells," *Cell Calcium* 11:323–327 (1990).

Neuvonen and Pihlaja, "Studies on the Benzoxazine Series. Part 3—Preparation and $^{13}C$ NMR Structural Study of γ Effects of Some N–Substituted 3,4–Dihydro–2H–1,3–benzoxazines," *Magnetic Resonance in Chemistry* 28:239–245 (1990).

Opie, "Calcium Channel Antagonists Part V: Second–Generation Agents," *Cardiovascular Drugs and Therapy* 2:191–203 (1988).

Paulsen–Sorman et al., "Cytochrome P–455 nm Complex Formation in the Metabolism of Phenylalkylamines. 8. Stereoselectivity in Metabolic Intermediary Complex Formation with a Series of Chiral 2–Substituted 1–Phenyl–2–aminoethanes," *J. Med. Chem.* 27:342–346 (1984).

Polniaszek and Dillard, "Diastereoselective Addition of Organometallic Reagents to Chiral Immune Ions: Synthesis of (S)–(+)–Cryptostyline I," *Tetrahedron Letters* 31:797–800 (1990).

Polniaszek and Kaufman, "Steroselective Nucleophilic Additions to the Carbon–Nitrogen Double Bond. 2. Chiral Iminium Ions Derived from "Second Generation" Chiral Amines," *J. Am. Chem. Soc.* 111:4859–4863 (1989).

Racke et al., "Functional expression of the parathyroid cell calcium receptor in Xenopus oocytes," *FEBS Letters* 333(1, 2):132–136 (1993).

Racke et al., "Functional Expression of the Parathyroid Cell Calcium Recptor in Xenopus Oocytes," *Journal of Bone and Mineral Research* Supplement 1, 6:S118 at abtract No. 141 (1991).

Rai et al., "Synthesis and reduction of ketimines," *Indian J. Chem.* 14B:377–378 (1976).

Rogers et al., "Calcium Receptor Expression in the Parathryoid Glands of Vitamin D–Deficient Rats is not Regulated by Plasma Caclium and $1,25(OH)_2D_3$," *Journal of Bone and Mineral Research* 9(1):S409 at abstract No. C392 (1994).

Rogers et al., "Localization of Calcium Receptor mRNA in Rat Thyoid and Parathyroid Glands Using In Situ Hybridization Histochemistry," *Journal Bone and Mineral Research* 9(1):S409 at abstract No. C390 (1994).

Rogers et al., "Pharmacological Comparison of Bovine Parathyroid, Human Parathyroid and Rat Kidney Calcium Receptors Expressed in HEK 293 Cells," *Journal of Bone and Mineral Research* 10(1):S483 (1995).

Rogers et al., "The Calcimimetic Compound NPS467 Reduces Plasma Calcium in a Dose–Dependent and Stero–Specific Manner," *Journal of Bone and Mineral Research* 8(Supplement 1):S180 at abstract No. 254 (1993).

Schäfer et al., "Polyamine Toxins from Spiders and Wasps," *The Alkaloids* 45:1–125 (1994).

Schwartz and Hu, "Synthesis of Hindered Secondary Amines via Grignard Reagent Addition to Ketonitrones," *Tetrahedron Letters* 13:1689–1692 (1992).

Seely et al., "The Calcium Channel Blocker Diltiazem Lowers Serum Parathyroid Hormone Levels in Vivo and in Vitro," *Journal of Clinical Endocrinology and Metabolism* 68(6):1007–1012 (1989).

Shafik et al., "Synthesis and characterization of some (±) 1–(Substituted amino or piperidino)–1–phenylethanes: Novel biososteric relatives of PCP," *J. Pharm. Sci.* 8(3):215–217 (1994).

Shafik et al., Chemical Abstracts, vol. 123 abstract 339222 (1995).

Shoback and Chen, "Injection of Poly $(A)^+$ RNA from Bovine Parathyroid Tissue into Xenopus Oocytes Confers Sensitivity to Extracellular Calcium," *Journal of Bone and Mineral Research* 6(Supplement 1):S135 at abstract No. 207 (1991).

Standridge et al., "Phenylalkylamines with Potential Psychotherapeutic Utility. 2. Nuclear Substituted 2–Amino–1–phenylbutanes," *J. Med. Chem.* 23:154–162 (1980).

Standridge et al., "Phenylalkylamines with Potential Psychotherapeutic Utility. 1. 2–Amino–1–(2, 5–dimethoxy–4–methylphenyl) butane," *J. Med. Chem.* 19:1400–1404 (1976).

Steffey and Nemeth, "Extracellular Calcium–Sensing Mechanisms on Osteoclasts and Parathyroid Cells are Pharmacologically Distinct," *Journal of Bone and Mineral Research* 8(Supplement 11):S384 at at abstract No. 1071 (1993).

Steffey et al., "Calcimimetics: Structually and Mechanistically Novel Compounds that Inhibit Hormone Secretion From Parathyroid Cells," *Journal of Bone and Mineral Research* 8(Supplement 1):S175 at abstract No. 236 (1993).

Takenaka et al., "Induced circular dichroism of chiral amine–benzoylbenzoic acid systems," J. Chem. Soc. Perkin Trans 2:95–99 (1978).

Triggle et al., "$Ca^{2+}$ Channel Ligands: Structure–Function Relationships of the 1,4–Dihydropyridines," *Medicinal Research Reviews* 9(2):123–180 (1989).

Van Dijk and Moed, "Synthesis of β–Phenylethyloamine Derivatives $X^{1*}$ N–(Hydroxy– and Methoxy–Aralkyl) Derivatives," *Recl. Trav. Chim. Pays–Bas* 92:1281–1297 (1973).

Van Niel and Pandit, "NADH Models XXI. Steroselective Reduction of Chiral Imines with Hantzsch Ester," *Tetrahedron* 41:6065–6011 (1985).

Walker et al., "Synthesis of varied heterocyclic and substituted aryl alkyl secondary amines, related schiff bases and amides," *J. Med. Chem.* 9(4):624–630 (1966).

Wang and Bäckvall, "Ruthenium–catalysed Transfer Hydrogenation of Imines by Propan–2–ol," *J. Chem. Soc. Commun.* pp. 980–982 (1992).

West et al., "A pharmacological study of a series of aralkyamines," J. Am. Pharm. Assoc. 46:58–61 (1957).

Witkop, "Nonenzymatic Methods for the Preferential and Selective Cleavage and Modification of Proteins," in *Advances in Protein Chemistry*, Anfinsen et al. editors, Academic Press, Inc., New York, 16:221–321 (1961).

Yamaguchi et al., "Asymmetric Reduction with Chiral Reagents from Lithium Aluminum Hydride and (S)–(–)–N–(o–Substituted benzyl)–α–phenylethylamines," *J. Org. Chem.* 42:1578–1581 (1977).

Zaidi et al., "Intracellular calcium in the control of osteoclast function. II. Paradoxical elevation of cytosolic free calcium by verapamil," *Biochemical and Biophysical Research Communications* 167:807–812 (1990).

Zaidi, "Calcium Receptors' on Eukaryotic Cells with Special Reference to the Osteoclast," *Bioscience Reports* 10:493–507 (1990).

\* cited by examiner

25Z

26F

26A

26G

6X

26H

26B

26I

26C

26J

26D

26K

26E

26L

26M

26T

26N

26U

26O

26V

26P

26W

26Q

26X

26R

26Y

26S

26Z

27G

27A

27H

27B

27I

27C

27J

27D

27K

27E

27L

27F

27M

INORGANIC ION RECEPTOR-ACTIVE COMPOUNDS

RELATED APPLICATIONS

This application is a continuation of U.S. patent application Ser. No. 09/415,179, filed on Oct. 6, 1999 which issued as U.S. Pat. No. 6,342,532, which is a divisional application of U.S. patent application Ser. No. 08/846,721, filed on Apr. 30, 1997 which issued as U.S. Pat. No. 5,981,599, and claims the benefit of provisional application U.S. Ser. No. 60/016,673 filed May 1, 1996, which is hereby incorporated herein in its entirety including the drawings.

FIELD OF THE INVENTION

This invention relates to compounds able to modulate one or more inorganic ion receptor activities.

BACKGROUND OF THE INVENTION

The references provided herein are not admitted to be prior art to the claimed invention.

Certain cells in the body respond not only to chemical signals, but also to ions such as extracellular calcium ions ($Ca^{2+}$). Extracellular $Ca^{2+}$ is under tight homeostatic control and regulates various processes such as blood clotting, nerve and muscle excitability, and proper bone formation.

Calcium receptor proteins enable certain specialized cells to respond to changes in extracellular $Ca^{2+}$ concentration. For example, extracellular $Ca^{2+}$ inhibits the secretion of parathyroid hormone (PTH) from parathyroid cells, inhibits bone resorption by osteoclasts, and stimulates secretion of calcitonin from C-cells.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. (Brown et al., *Nature* 366:574, 1993.) In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ can exert effects on different cell functions, reviewed in Nemeth et al., *Cell Calcium* 11:319, 1990. The role of extracellular $Ca^{2+}$ in parafollicular (C-cells) and parathyroid cells is discussed in Nemeth, *Cell Calcium* 11:323, 1990. These cells were shown to express similar calcium receptors. (See Brown et al., *Nature* 366:574, 1993; Mithal et al., *J. Bone Miner. Res.* 9, Suppl. 1, s282, 1994; Rogers et al., *J. Bone Miner. Res.* 9, Suppl, 1, s409, 1994; Garrett et al., *Endocrinology* 136:5202–5211, 1995.)

The ability of various molecules to mimic extracellular $Ca^{2+}$ in vitro is discussed in references such as Nemeth et al., in "Calcium-Binding Proteins in Health and Disease," 1987, Academic Press, Inc., pp. 33–35; Brown et al., *Endocrinology* 128:3047, 1991; Chen et al., *J. Bone Miner. Res.* 5:581, 1990; and Zaidi et al., *Biochem. Biophys. Res. Commun.* 167:807, 1990.

Nemeth et al., PCT/US92/07175, International Publication Number WO 93/04373, Nemeth et al., PCT/US93/01642, International Publication Number WO 94/18959, and Nemeth et al., PCT/US94/12117, International Publication Number WO 95/11211, describe various compounds which can modulate the effect of an inorganic ion receptor.

SUMMARY OF THE INVENTION

The present invention features compounds able to modulate one or more activities of an inorganic ion receptor and methods for treating diseases or disorders using such compounds. Preferred compounds can mimic or block the effect of extracellular calcium on a cell surface calcium receptor.

Inorganic ion receptor activities are those processes brought about as a result of inorganic ion receptor activation. Such processes include the production of molecules which can act as intracellular or extracellular messengers.

Inorganic ion receptor-modulating compounds include ionomimetics, ionolytics, calcimimetics, and calcilytics. Ionomimetics are compounds which mimic (i.e., evoke or potentiate) the effects of an inorganic ion at an inorganic ion receptor. Preferably, the compound affects one or more calcium receptor activities. Calcimimetics are ionomimetics which affect one or more calcium receptor activities.

Ionolytics are compounds which block (i.e., inhibit or diminish) one or more activities caused by an inorganic ion at an inorganic ion receptor. Preferably, the compound affects one or more calcium receptor activities. Calcilytics are ionolytics which block one or more calcium receptor activities evoked by extracellular calcium.

Ionomimetics and ionolytics may bind at the same receptor site as the native inorganic ion ligand binds or can bind at a different site (e.g., an allosteric site). For example, NPS R-467 binding to a calcium receptor results in calcium receptor activity and, thus, NPS R-467 is classified as a calcimimetic. However, NPS R-467 binds to the calcium receptor at a different site (i.e., an allosteric site) than extracellular calcium.

A measure of the effectiveness of a compound to modulate receptor activity can be determined by calculating the $EC_{50}$ or $IC_{50}$ for that compound. The $EC_{50}$ is the concentration of a compound which causes a half-maximal mimicking effect. The $IC_{50}$ is the concentration of a compound which causes a half-maximal blocking effect. $EC_{50}$ and $IC_{50}$ values for compounds at a calcium receptor can be determined by assaying one or more of the activities of extracellular calcium at a calcium receptor. Examples of assays for measuring $EC_{50}$ and $IC_{50}$ values are described Nemeth et al., PCT/US93/01642, International Publication Number WO 94/18959, and Nemeth et al., PCT/US92/07175, International Publication Number WO 93/04373, (both of these publications are hereby incorporated by reference here) and below. Such assays include oocyte expression assays and measuring increases in intracellular calcium ion concentration ($[Ca^{2+}]_i$) due to calcium receptor activity. Preferably, such assays measure the release or inhibition of a particular hormone associated with activity of a calcium receptor.

An inorganic ion receptor-modulating compound preferably selectively targets inorganic ion receptor activity in a particular cell. For example, selective targeting of a calcium receptor activity is achieved by a compound exerting a greater effect on a calcium receptor activity in one cell type than at another cell type for a given concentration of compound. Preferably, the differential effect is 10-fold or greater as measured in vivo or in vitro. More preferably, the differential effect is measured in vivo and the compound concentration is measured as the plasma concentration or extracellular fluid concentration and the measured effect is the production of extracellular messengers such as plasma calcitonin, parathyroid hormone, or plasma calcium. For example, in a preferred embodiment, the compound selectively targets PTH secretion over calcitonin secretion.

Preferably, the compound is either a calcimimetic or calcilytic having an $EC_{50}$ or an $IC_{50}$ at a calcium receptor of less than or equal to 5 $\mu$M, and even more preferably less than or equal to 1 $\mu$M, 100 nmolar, 10 nmolar, or 1 nmolar using one of the assays described below. More preferably, the assay measures intracellular $Ca^{2+}$ in HEK 293 cells transformed with nucleic acid expressing the human parathyroid calcium receptor and loaded with fura-2. Lower $EC_{50}$ or $IC_{50}$ values are advantageous since they allow lower concentrations of compounds to be used in vivo or in vitro. The discovery of compounds with low $EC_{50}$ and $IC_{50}$ values enables the design and synthesis of additional compounds having similar or improved potency, effectiveness, and/or selectivity.

Thus, a first aspect the invention features an inorganic ion receptor-modulating compound having the formula:

STRUCTURE I

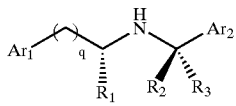

wherein $Ar_1$ is either optionally substituted naphthyl, optionally substituted phenyl, or an optionally substituted heterocyclic aryl, where up to 5 substituents may be present and each substituent is independently selected from the group consisting of: alkyl, alkenyl, halogen, alkoxy, thioalkyl, methylene dioxy, haloalkyl, haloalkoxy, OH, $CH_2OH$, $CONH_2$, CN, acetoxy, $N(alkyl)_2$, phenyl, phenoxy, benzyl, benzyloxy, $\alpha,\alpha$-dimethylbenzyl, $NO_2$, CHO, $CH_3CH(OH)$, acetyl, $OCH_2COOH$, and ethylene dioxy;

$Ar_2$ is either optionally substituted naphthyl, optionally substituted phenyl, or an optionally substituted heterocyclic aryl, where up to 5 substituents may be present and each substituent is independently selected from the group consisting of: alkyl, alkenyl, halogen, alkoxy, thioalkyl, methylene dioxy, haloalkyl, haloalkoxy, OH, $CH_2OH$, $CONH_2$, CN, $OCH_2COOH$, ethylene dioxy, and acetoxy;

q is 0, 1, 2, or 3;

$R_1$ is either H or alkyl; and $R_2$ and $R_3$ are each independently either hydrogen, alkyl, or together cycloalkyl or cycloalkenyl;

and pharmaceutically acceptable salts and complexes thereof.

Preferably, the compound is an ionomimetic which modulates one or more inorganic ion receptor activities, more preferably the compound is a calcimimetic.

"Alkenyl" refers to a hydrocarbon chain having 2–6 carbons and at least one double-bond which may be a straight chain, branched, or non-aromatic cyclic. Preferably, the alkenyl has 2–4 carbon atoms.

"Alkyl" refers to a saturated hydrocarbon having 1–6 carbons which may be a straight chain, branched, or cyclic. Preferably, the alkyl has 1–4 carbon atoms.

"Alkoxy" refers to "O-alkyl," where "O" is an oxygen joined to an alkyl.

"Cycloalkenyl" refers to a non-aromatic cyclic hydrocarbon chain having 3–12 carbons and at least one double-bond, and includes multiple ring structures. Preferably, the cycloalkenyl has 3 to 6 carbon atoms.

"Cycloalkyl" refers to a saturated cyclic hydrocarbon chain having 3–12 carbons, and includes multiple ring structures. Preferably, the cycloalkyl has 3 to 6 carbon atoms.

"Thioalkyl" refers to "S-alkyl," where "S" is a sulfur joined to an alkyl.

"Haloalkyl" refers to an alkyl substituted with at least one halogen. Preferably, only the terminal carbon of the haloalkyl is substituted with a halogen and 1 to 3 halogens are present. More preferably, the haloalkyl contains 1 carbon. Preferably, the halogen substitutions are either Cl or F.

"Haloalkoxy" refers to "O-haloalkyl," where "O" is an oxygen joined to a haloalkyl.

"Heterocyclic aryl" refers to an aryl ring system having 1 to 3 heteroatoms as ring atoms in a heteroaromatic ring system and the remainder of the ring atoms are carbon atoms. Suitable heteroatoms include oxygen, sulfur, and nitrogen. Preferably, the heterocyclic aryl ring system is mono- or bicyclic. More preferably, the heterocyclic aryl is either furanyl, thiofuranyl (also known as "thienyl"), benzofuranyl or benzothiofuranyl (also known as "benzothienyl").

Another aspect of the present invention features an inorganic ion receptor-modulating compound having the formula:

STRUCTURE II

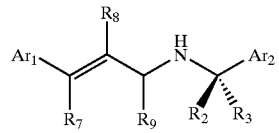

Where $Ar_1$, $Ar_2$, $R_2$ and $R_3$ are as described for Structure I compounds;

$R_7$ is either hydrogen, alkyl or phenyl;

$R_8$ is either hydrogen, or alkyl;

$R_9$ is either hydrogen, alkyl or phenyl; and pharmaceutically acceptable salts and complexes thereof.

Preferably, the compound is an ionomimetic modulating one or more inorganic ion receptor activities, more preferably the compound is a calcimimetic.

Another aspect of the present invention features a pharmaceutical composition made up of an inorganic ion receptor-modulating compound described herein and a physiologically acceptable carrier. A "pharmacological composition" refers to a composition in a form suitable for administration into a mammal, preferably a human. Preferably, the pharmaceutical composition contains a sufficient amount of a calcium receptor-modulating compound in a proper pharmaceutical form to exert a therapeutic effect on a human.

Considerations concerning forms suitable for administration are known in the art and include toxic effects, solubility, route of administration, and maintaining activity. For example, pharmacological compositions injected into the blood stream should be soluble.

Pharmaceutical compositions can also be formulated as pharmaceutically acceptable salts (e.g., acid addition salts) and complexes thereof. The preparation of such salts can facilitate the pharmacological use of a compound by altering its physical characteristics without preventing it from exerting a physiological effect.

Another aspect the present invention features a method for treating a patient by using inorganic ion receptor-modulating compounds described herein. The method involves administering to the patient a pharmaceutical composition containing a therapeutically effective amount of an inorganic ion receptor-modulating compound. In a preferred embodiment, the disease or disorder is treated by administering to the patient a therapeutically effective amount of a calcium receptor-modulating compound.

Inorganic ion receptor-modulating compounds, and compositions containing such compounds, can be used to treat different types of patients. A "patient" refers to a mammal in which compounds able to modulate inorganic ion receptor activity will have a beneficial effect including a beneficial prophylactic effect. Suitable patients can be diagnosed using standard techniques known to those in the medical profession.

Preferably, a patient is a human having a disease or disorder characterized by one more of the following: (1) abnormal inorganic ion homeostasis, more preferably abnormal calcium homeostasis; (2) an abnormal level of a messenger whose production or secretion is affected by inorganic ion receptor activity, more preferably affected by calcium receptor activity; and (3) an abnormal level or activity of a messenger whose function is affected by inorganic ion receptor activity, more preferably affected by calcium receptor activity.

Diseases characterized by abnormal calcium homeostasis include hyperparathyroidism, osteoporosis and other bone and mineral-related disorders, and the like (as described, e.g., in standard medical text books, such as "Harrison's Principles of Internal Medicine"). Such diseases are treated using calcium receptor-modulating compounds which mimic or block one or more of the effects of extracellular $Ca^{2+}$ on a calcium receptor.

By "therapeutically effective amount" is meant an amount of a compound which relieves to some extent one or more symptoms of a disease or disorder in the patient; or returns to normal either partially or completely one or more physiological or biochemical parameters associated with or causative of the disease or disorder. Thus, a therapeutically effective amount can be an amount effective to prophylactically decrease the likelihood of the onset of a disease or disorder.

In a preferred embodiment, the patient has a disease or disorder characterized by an abnormal level of one or more calcium receptor-regulated components and the compound is active on a calcium receptor of a cell selected from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell, and cell of the subformical organ.

More preferably, the cells are chosen from the group consisting of: parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell, and cell of the subformical organ.

In a preferred embodiment, the compound reduces the level of parathyroid hormone in the serum of the patient. More preferably, the level is reduced to a degree sufficient to cause a decrease in plasma $Ca^{2+}$. Most preferably, the parathyroid hormone level is reduced to that present in a normal individual.

Patients in need of treatment using the compounds described by the present invention can be diagnosed by standard medical techniques, such as blood or urine analysis. Examples of such medical techniques include detecting a deficiency of protein whose production or secretion is affected by changes in inorganic ion concentrations, and by detecting abnormal levels of inorganic ions or hormones which effect inorganic ion homeostasis.

Various examples are used throughout the application. These examples are not intended in any way to limit the claimed invention.

Other features and advantages of the invention will be apparent from the following figures, detailed description of the invention, examples, and the claims.

DESCRIPTION OF THE PREFERRED EMBODIMENTS

Figure 1A:
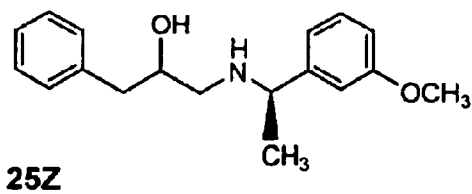
FIG. 1 provides the chemical structures of different ionomimetic compounds.
Figure 1A:
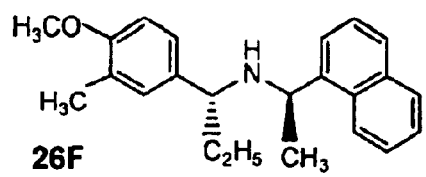
Figure 1A:
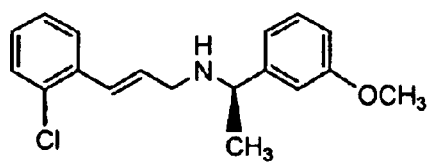
Figure 1A:
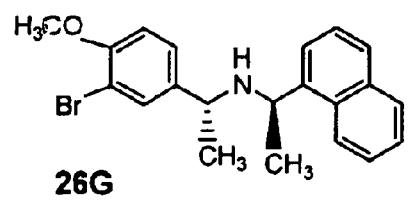
Figure 1A:
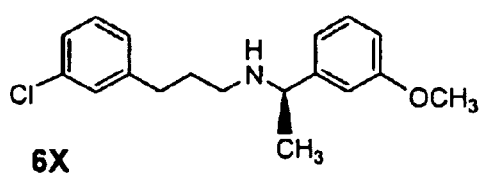
Figure 1A:
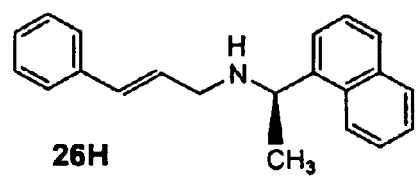
Figure 1A:
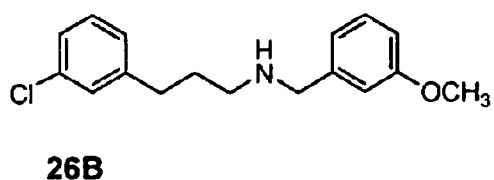
Figure 1A:
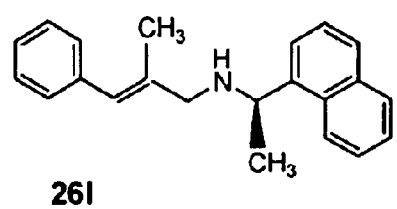
Figure 1A:
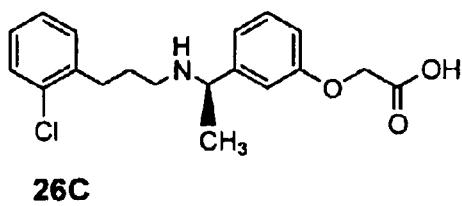
Figure 1A:
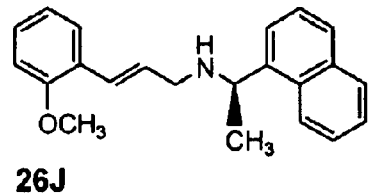
Figure 1A:
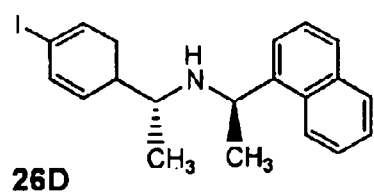
Figure 1A:
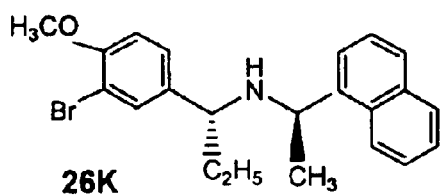
Figure 1A:
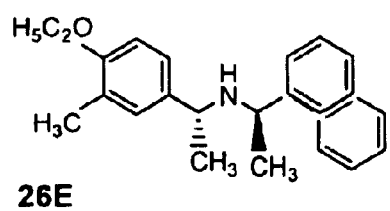
Figure 1A:
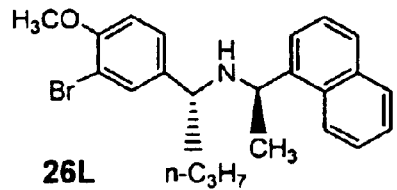
Figure 1B:
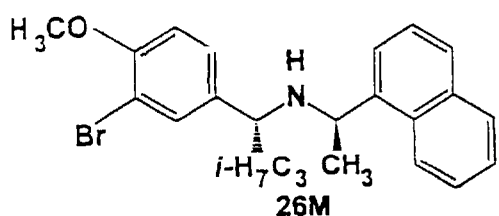
Figure 1B:
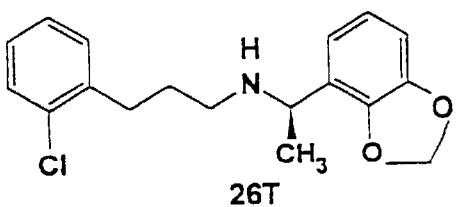
Figure 1B:
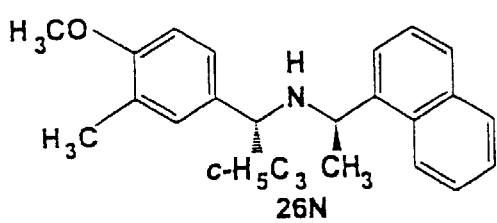
Figure 1B:
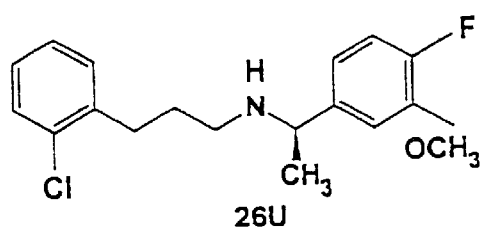
Figure 1B:
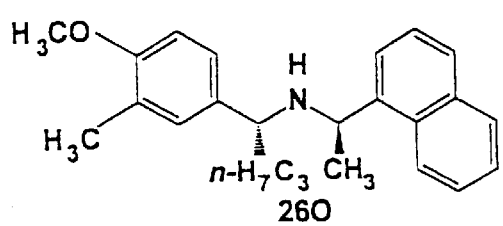
Figure 1B:
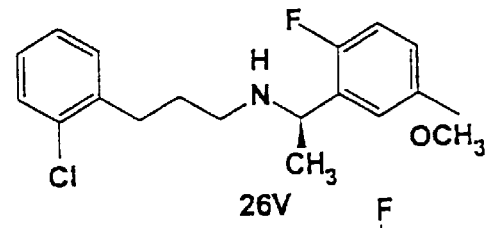
Figure 1B:
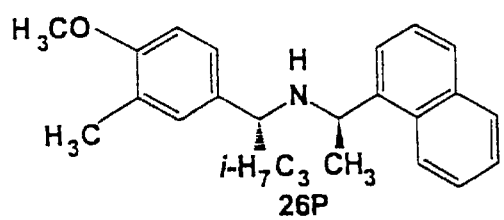
Figure 1B:
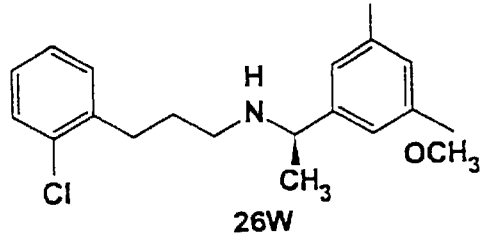
Figure 1B:
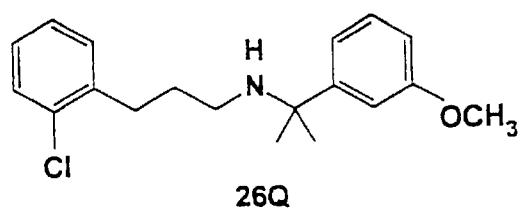
Figure 1B:
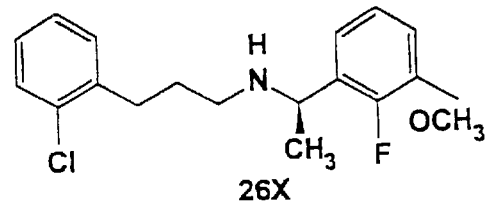
Figure 1B:
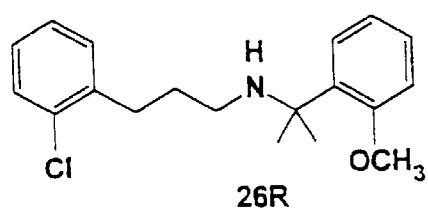
Figure 1B:
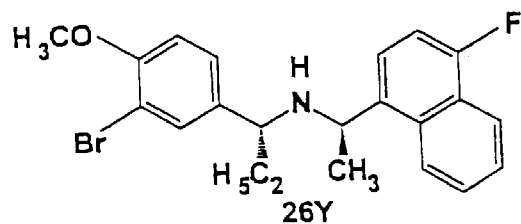
Figure 1B:
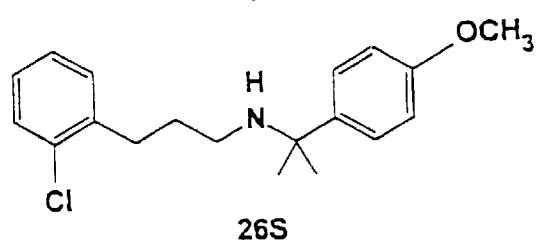
Figure 2:
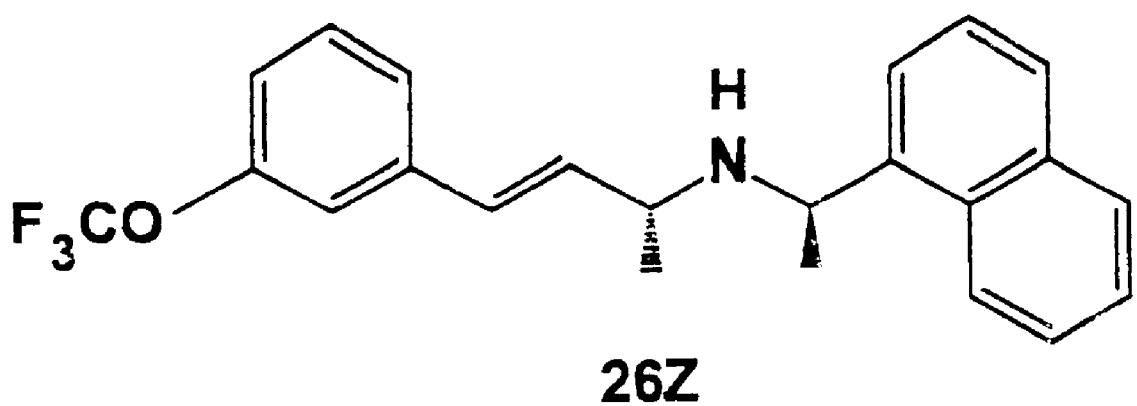
FIG. 2 provides the chemical structure of an ionomimetic compound.
Figure 3A:
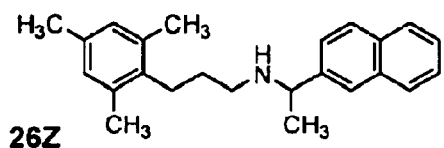
FIG. 3 provides the chemical structures of different ionomimetic compounds.
Figure 3A:
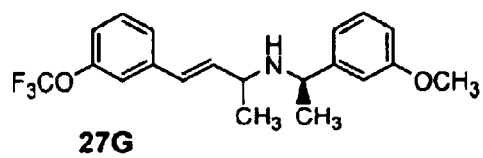
Figure 3A:
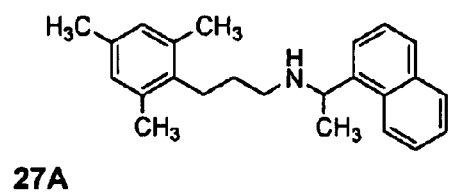
Figure 3A:
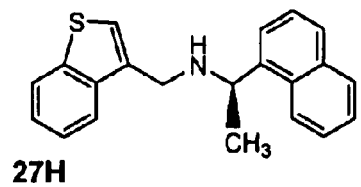
Figure 3A:
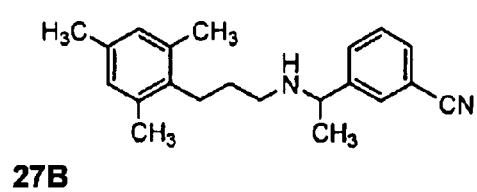
Figure 3A:
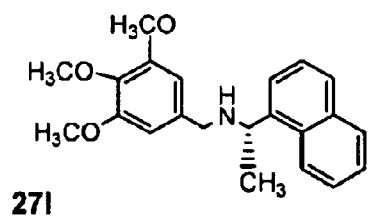
Figure 3A:
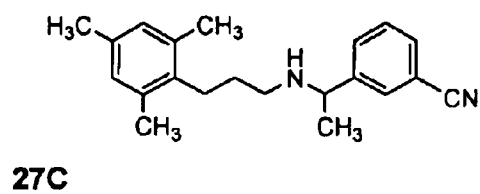
Figure 3A:
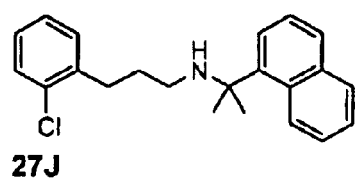
Figure 3A:
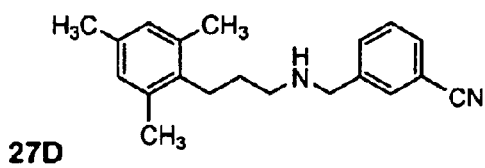
Figure 3A:
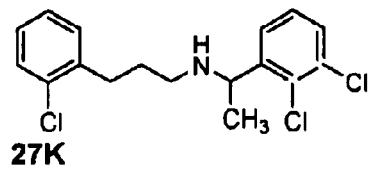
Figure 3A:
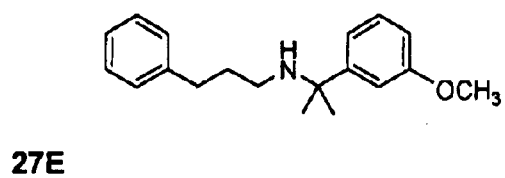
Figure 3A:
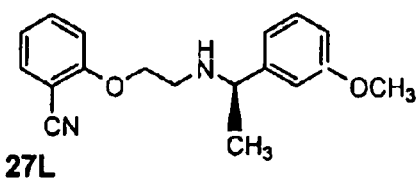
Figure 3A:
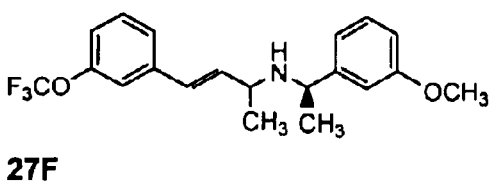
Figure 3A:
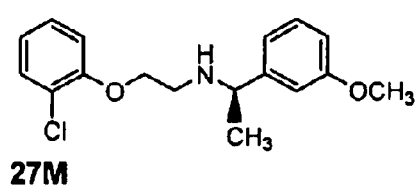
Figure 3B:
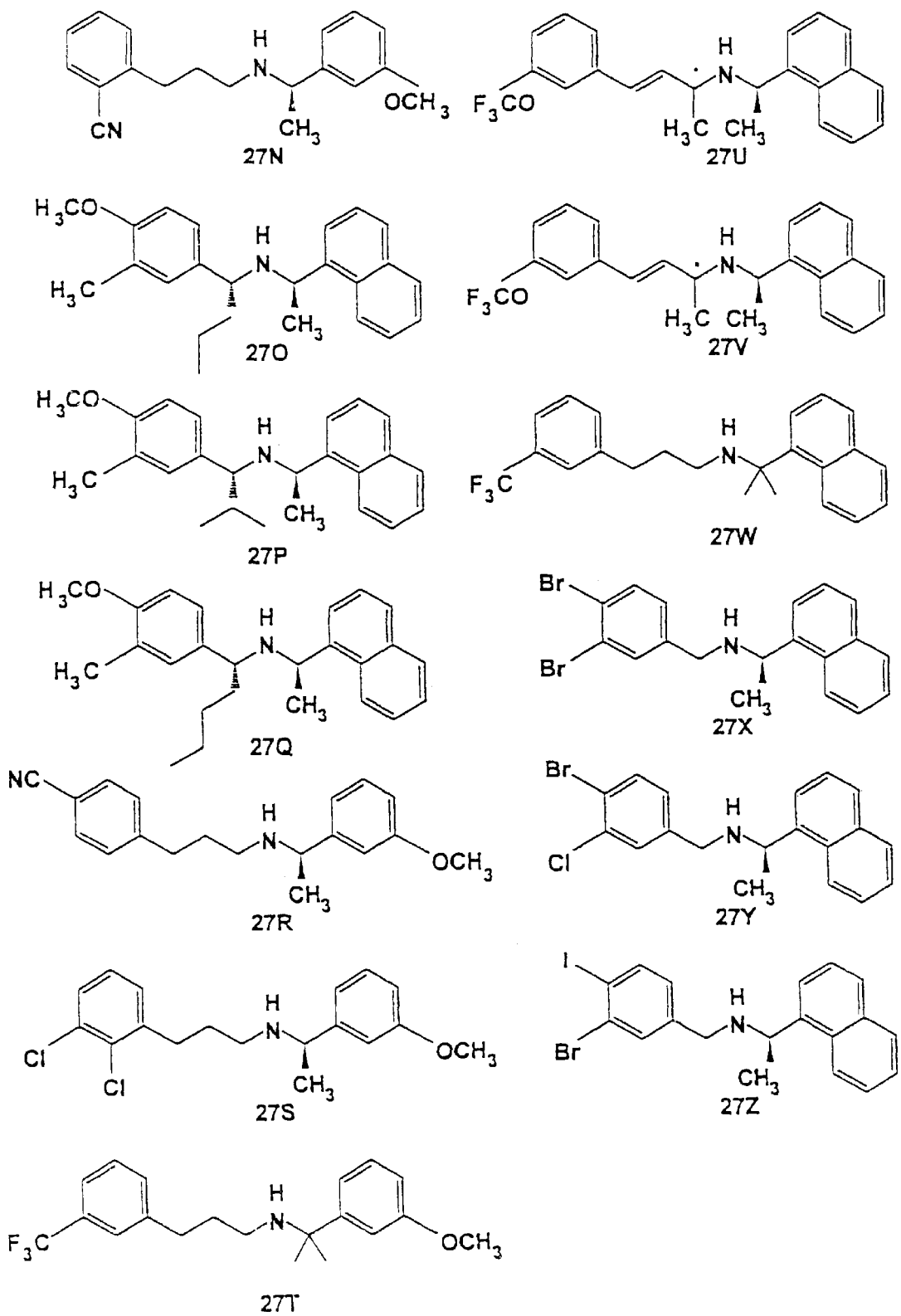
Figure 4:
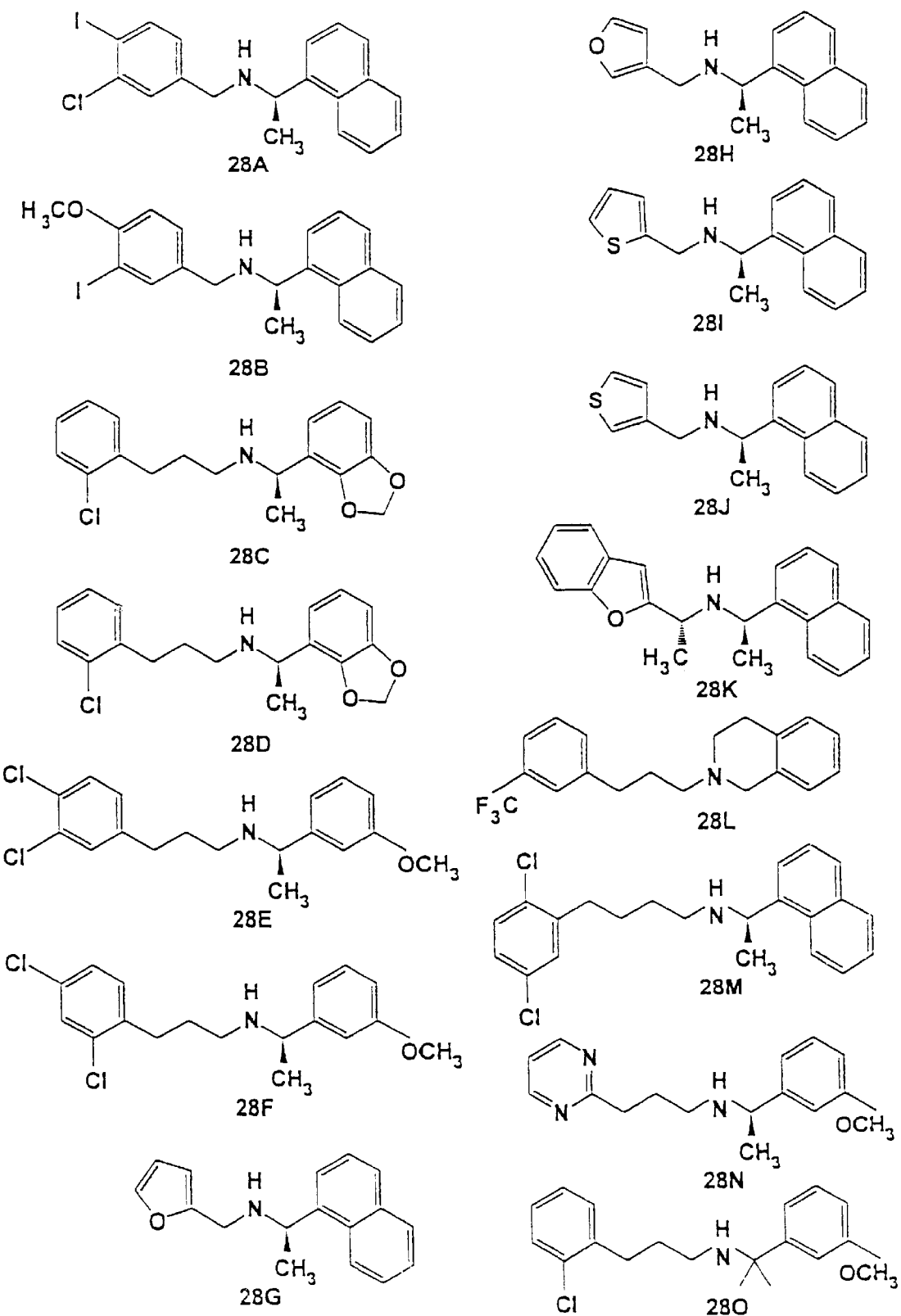
FIG. 4 provides the chemical structures of different ionomimetic compounds.

The present invention features compounds able to modulate one or more inorganic ion receptor activities. Preferably, the compounds can mimic or block an effect of an extracellular ion on a cell having an inorganic ion receptor, more preferably, the extracellular ion is $Ca^{2+}$ and the effect is on a cell having a calcium receptor. Most preferably, the compounds can mimic the effect of extracellular $Ca^{2+}$ on a cell having a calcium receptor.

While the compounds described herein are believed to be able to act at an inorganic ion receptor, preferably a calcium receptor, unless otherwise explicitly stated in the claims that a compound exerts an effect by acting at a receptor, there is no intention to limit the claimed methods to those requiring modulation of receptor activity. Rather, the compounds are characterized by their ability to modulate inorganic ion receptor activity in vivo or in vitro.

I. Calcium Receptors

Calcium receptors are present in different cells. The pharmacological effects of the following cells, in response to extracellular $Ca^{2+}$, is consistent with the presence of a calcium receptor: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, endocrine and exocrine cells in the pancreas, fat/adipose cell, immune cell, GI tract cell, skin cell, adrenal cell, pituitary cell, hypothalamic cell, and cell of the subformical organ.

The presence of a calcium receptor on the following cells have been confirmed using physical data, such as hybridization with nucleic acid encoding a calcium receptor: parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell, cell of the subformical organ, and endocrine and exocrine cells in the pancreas.

The calcium receptor on these different cell types may be different. It is also possible that a cell can have more than one type of calcium receptor. Comparison of calcium receptor activities and amino acid sequences from different cells indicate that distinct calcium receptor types exist. For example, calcium receptors can respond to a variety of di- and trivalent cations. The parathyroid cell calcium receptor responds to calcium and $Gd^{3+}$, while osteoclasts respond to divalent cations such as calcium, but do not respond to $Gd^{3+}$. Thus, the parathyroid cell calcium receptor is pharmacologically distinct from the calcium receptor on the osteoclast.

On the other hand, the nucleic acid sequences encoding calcium receptors present in parathyroid cells and C-cells indicate that these receptors have a very similar amino acid structure. Nevertheless, calcimimetic compounds exhibit differential pharmacology and regulate different activities at parathyroid cells and C-cells. Thus, pharmacological properties of calcium receptors may vary significantly depending upon the cell type or organ in which they are expressed even though the calcium receptors may have similar or even identical structures.

Calcium receptors, in general, have a low affinity for extracellular $Ca^{2+}$ (apparent $K_d$ generally greater than about 0.5 mM). Calcium receptors may include a free or bound effector mechanism as defined by Cooper, Bloom and Roth, "The Biochemical Basis of Neuropharmacology", Ch. 4, and are thus distinct from intracellular calcium receptors, e.g., calmodulin and the troponins.

Calcium receptors respond to changes in extracellular calcium levels. The exact changes depend on the particular receptor and cell line containing the receptor. For example, the in vitro effect of calcium on the calcium receptor in a parathyroid cell includes the following:

1. An increase in internal calcium. The increase is due to the influx of external calcium and/or to mobilization of internal calcium. Characteristics of the increase in internal calcium include the following:
   (a) A rapid (time to peak <5 seconds) and transient increase in $[Ca^{2+}]_i$ that is refractory to inhibition by 1 μM $La^{3+}$ or 1 μM $Gd^{3+}$ and is abolished by pretreatment with ionomycin (in the absence of extracellular $Ca^{2+}$);
   (b) The increase is not inhibited by dihydropyridines;
   (c) The transient increase is abolished by pretreatment for 10 minutes with 10 mM sodium fluoride;
   (d) The transient increase is diminished by pretreatment with an activator of protein kinase C (PKC), such as phorbol myristate acetate (PMA), mezerein or (–)-indolactam V. The overall effect of the protein kinase C activator is to shift the concentration-response curve of calcium to the right without affecting the maximal response; and
   (e) Pretreatment with pertussis toxin (100 ng/ml for >4 hours) does not affect the increase.

2. A rapid (<30 seconds) increase in the formation of inositol-1,4,5-triphosphate or diacylglycerol. Pretreatment with pertussis toxin (100 ng/ml for >4 hours) does not affect this increase;

3. The inhibition of dopamine- and isoproterenol-stimulated cyclic AMP formation. This effect is blocked by pretreatment with pertussis toxin (100 ng/ml for >4 hours); and 4. The inhibition of PTH secretion. Pretreatment with pertussis toxin (100 ng/ml for >4 hours) does not affect the inhibition in PTH secretion.

Using techniques known in the art, the effect of calcium on other calcium receptors in different cells can be readily determined. Such effects may be similar in regard to the increase in internal calcium observed in parathyroid cells. However, the effect is expected to differ in other aspects, such as causing or inhibiting the release of a hormone other than parathyroid hormone.

II. Inorganic Ion Receptor-Modulating Compounds

Inorganic ion receptor-modulating compounds modulate one or more inorganic ion receptor activities. Preferred inorganic ion receptor-modulating compounds are calcimimetics or calcilytics. Inorganic ion receptor-modulating compounds can be identified by screening compounds which are modeled after a compound shown to have a particular activity (i.e., a lead compound).

A preferred method of measuring calcium receptor activity is to measure changes in $[Ca^{2+}]_i$. Changes in $[Ca^{2+}]_i$ can be measured using different techniques such as by using HEK 293 cells transduced with nucleic acid expressing the human parathyroid calcium receptor and loaded with fura-2; and by measuring an increase in $Cl^-$ current in a Xenopus oocyte injected with nucleic acid coding for a calcium receptor. (See Nemeth et al., PCT/US93/01642, International Publication Number WO 94/18959.) For example, poly(A)$^+$ mRNA can be obtained from cells expressing a calcium receptor, such as a parathyroid cell, bone osteoclast, juxtaglomerular kidney cell, proximal tubule kidney cell, distal tubule kidney cell, cell of the thick ascending limb of Henle's loop and/or collecting duct, keratinocyte in the epidermis, parafollicular cell in the thyroid (C-cell), intestinal cell, central nervous cell, peripheral nervous system cell, platelet, vascular smooth muscle cell, cardiac atrial cell, gastrin-secreting cell, glucagon-secreting cell, kidney mesangial cell, mammary cell, beta cell, fat/adipose cell, immune cell, and GI tract cell. Preferably, the nucleic acid is from a parathyroid cell, C-cell, or osteoclast. More preferably, the nucleic acid encodes a calcium receptor and is present on a plasmid or vector.

In a preferred embodiment, the compound has an $EC_{50}$ or $IC_{50}$ less than or equal to 5 μM at one or more, but not all cells chosen from the group consisting of: parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, platelet, vascular smooth muscle cell, cardiac atrial cell, gastrin-secreting cell, glucagon-secreting cell, kidney mesangial cell, mammary cell, beta cell, fat/adipose cell, immune cell, GI tract cell, skin cell, adrenal cell, pituitary cell, hypothalamic cell, and cell of the subformical organ. More preferably, the cells are chosen from the group consisting of parathyroid cell, central nervous system cell, peripheral nervous system cell, cell of the thick ascending limb of Henle's loop and/or collecting duct in the kidney, parafollicular cell in the thyroid (C-cell), intestinal cell, GI tract cell, pituitary cell, hypothalamic cell, and cell of the subformical organ. The presence of a calcium receptor in this group of cells has been confirmed by physical data such as in situ hybridization and antibody staining.

Preferably, inorganic ion receptor-modulating compounds mimic or block the effects of an extracellular ion on a cell having an inorganic ion receptor, such that the compounds achieve a therapeutic effect. Inorganic ion receptor-modulating compounds may have the same, or different, effects on cells having different types of inorganic ion receptor morphology (e.g., such as cells having normal inorganic ion receptors, a normal number of inorganic ion receptors, an abnormal inorganic ion receptor, and an abnormal number of inorganic ion receptors).

Calcium receptor-modulating compounds preferably mimic or block all of the effects of extracellular ion in a cell having a calcium receptor. However, calcimimetics need not possess all the biological activities of extracellular $Ca^{2+}$. Similarly, calcilytics need not block all of the activities caused by extracellular calcium. Additionally, different calcimimetics and different calcilytics do not need to bind to the same site on the calcium receptor as does extracellular $Ca^{2+}$ to exert their effects.

Inorganic receptor-modulating compounds need not effect inorganic receptor activity to the same extent or in exactly the same manner as the natural ligand. For example, a calcimimetic may affect calcium receptor activity to a different extent, to a different duration, by binding to a different binding site, or by having a different affinity, compared to calcium acting at a calcium receptor.

A. Ionomimetics

Different compound are described by Nemeth et al., PCT/US92/07175, International Publication Number WO 93/04373, Nemeth et al., PCT/US93/01642, International Publication Number WO 94/18959, Nemeth et al., PCT/US94/12117, International Publication Number WO 95/11211, and Van Wagenen et al. PCT/US95/13704 (each of these references are hereby incorporated by reference herein). Different generic groups are described herein, preferably, these groups exclude each of the specific compounds described in these prior international applications (i.e., the specific compounds described in PCT/US92/07175, PCT/US93/01642, PCT/US94/12117, and PCT/US95/13704, are preferably excluded from the different generic and subgeneric formula provided herein).

1. Structure I Compounds

Structure I compounds able to modulate calcium receptor activity have the following formula:

STRUCTURE I

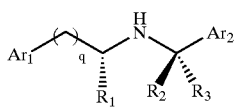

Where $Ar_1$ is either optionally substituted naphthyl, optionally substituted phenyl, or an optionally substituted heterocyclic aryl, where up to 5 substituents may be present and each substituent is independently selected from the group consisting of: alkyl, alkenyl, halogen, alkoxy, thioalkyl, methylene dioxy, haloalkyl, haloalkoxy, OH, $CH_2OH$, $CONH_2$, CN, acetoxy, $N(alkyl)_2$, phenyl, phenoxy, benzyl, benzyloxy, α,α-dimethylbenzyl, $NO_2$, CHO, $CH_3CH(OH)$, acetyl, $OCH_2COOH$, and ethylene dioxy. In one embodiment of the present invention $Ar_1$ is either an optionally substituted naphthyl, or a substituted phenyl, having 1 to 4 substituents, more preferably $Ar_1$ is either an unsubstituted naphthyl or a substituted phenyl; more preferably, $Ar_1$ is a substituted phenyl; preferably each $Ar_1$ substituent is independently selected from the group consisting of: isopropyl, $CH_3O$, $CF_3$ $CH_3S$, $CF_3O$, Br, I, Cl, F, and $CH_3$. In another embodiment of the present invention $Ar_1$ is an optionally substituted heterocyclic aryl. Preferred heterocyclic aryl substituents are independently selected from the group consisting of: isopropyl, $CH_3O$, $CF_3$ $CH_3S$, $CF_3O$, Br, I, Cl, F, and $CH_3$. Preferred heterocyclic aryls are either furanyl, thiofuranyl, benzofuranyl, or benzothiophenyl;

$Ar_2$ is either optionally substituted naphthyl, optionally substituted phenyl, or an optionally substituted heterocyclic aryl, where up to 5 substituents may be present and each substituent is independently selected from the group consisting of: alkyl, alkenyl, halogen, alkoxy, thioalkyl, methylene dioxy, haloalkyl, haloalkoxy, OH, $CH_2OH$, $CONH_2$, CN, $OCH_2COOH$, ethylene dioxy, and acetoxy; In one embodiment $Ar_2$ is preferably either an optionally substituted naphthyl, or a substituted phenyl having 1 to 4 substituents, more preferably $Ar_2$ is either an unsubstituted naphthyl or a substituted phenyl; more preferably, $Ar_2$ is a substituted phenyl with a substituent in the meta position, even more preferably, $Ar_2$ is mono substituted with a substituent in the meta position; preferably each $Ar_2$ substituent is independently selected from the group consisting of: isopropyl, $CH_3O$, $CH_3S$, $CF_3O$, Br, I, Cl, F, $CF_3$, and $CH_3$, more preferably a $CH_3O$ is located in the meta position. In another embodiment of the present invention $Ar_2$ is an optionally substituted heterocyclic aryl. Preferred heterocyclic aryl substituents are independently selected from the group consisting of: isopropyl, $CH_3O$, $CF_3$ $CH_3S$, $CF_3O$, Br, I, Cl, F, and $CH_3$. Preferred heterocyclic aryls are either furanyl, thiofuranyl, benzofuranyl, or benzothiophenyl;

q is 0, 1, 2, or 3; in alternative embodiments q is 0 or 2;

$R_1$ is either H or alkyl; when $R_1$ is alkyl in alternative embodiments the alkyl is methyl, or the alkyl has more than one carbon atom, preferably 2 to 4 carbon atoms;

$R_2$ and $R_3$ are each independently either hydrogen, alkyl, or together cycloalkyl or cycloalkenyl; preferably, $R_2$ and $R_3$ are each independently either hydrogen or alkyl, provided that at least one of $R_2$ and $R_3$ is not hydrogen, preferably, $R_2$ is alkyl, more preferably $R_2$ is methyl; and pharmaceutically acceptable salts and complexes thereof.

In a more preferred embodiment the compound has following formula:

STRUCTURE IA

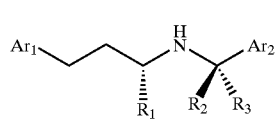

Where $Ar_1$, $Ar_2$, $R_1$, $R_2$, and $R_3$ are as described above for Structure I compounds, including preferred embodiments.

In another more preferred embodiment the compound has the formula:

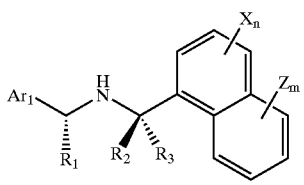

STRUCTURE IB

Where $Ar_1$, $R_1$, $R_2$, and $R_3$ is as described above for Structure I compounds including preferred embodiments;

each X and Z is independently selected from the group consisting of: alkyl, alkenyl, halogen, alkoxy, thioalkyl, methylene dioxy, haloalkyl, haloalkoxy, OH, $CH_2OH$, $CONH_2$, CN, $OCH_2COOH$, ethylene dioxy, and acetoxy; more preferably each X and Z is independently selected from the group consisting of: isopropyl, $CH_3O$, $CH_3S$, $CF_3O$, Br, I, Cl, F, $CF_3$, and $CH_3$;

n and m are each independently 0, 1, 2, or 3, provided that n and m together are no more than 5; preferably n and m are each independently 0 or 1, more preferably, 0.

2. Structure II Compounds

Structure II compounds have the formula:

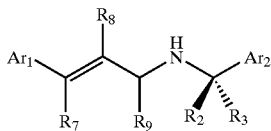

STRUCTURE II

Where $Ar_1$, $Ar_2$, $R_3$ and $R_4$ are as described above for Structure I compounds, including preferred embodiments;

$R_7$ is either hydrogen, alkyl or phenyl; preferably hydrogen;

$R_8$ is either hydrogen, or alkyl; preferably hydrogen;

$R_9$ is either hydrogen, alkyl or phenyl; preferably hydrogen or alkyl, when $R_9$ is alkyl in alternative embodiments the alkyl is methyl, or the alkyl has more than one carbon atom, preferably 2 to 4 carbon atoms;

and pharmaceutically acceptable salts and complexes thereof.

3. Calcimimetic Activity

The ability of compounds to mimic the activity of $Ca^{2+}$ at calcium receptors can be determined using procedures known in the art such as those described by Nemeth et al., PCT/US93/01642, International Publication Number WO 94/18959. For example, calcimimetics possess one or more and preferably all of the following activities when tested on parathyroid cells in vitro:

1. The compound causes a rapid (time to peak <5 seconds) and transient increase in intracellular calcium concentration that is refractory to inhibition by 1 μM $La^{3+}$ or 1 μM $Gd^{3+}$. The increase in $[Ca^{2+}]_i$ persists in the absence of extracellular $Ca^{2+}$, but is abolished by pretreatment with ionomycin (in the absence of extracellular $Ca^{2+}$);
2. The compound potentiates increases in $[Ca^{2+}]_i$ elicited by submaximal concentrations of extracellular $Ca^{2+}$;
3. The increase in $[Ca^{2+}]_i$ elicited by extracellular $Ca^{2+}$ is not inhibited by dihydropyridines;
4. The transient increase in $[Ca^{2+}]_i$ caused by the compound is abolished by pretreatment for 10 minutes with 10 mM sodium fluoride;
5. The transient increase in $[Ca^{2+}]_i$ caused by the compound is diminished by pretreatment with an activator of protein kinase C (PKC), such as phorbol myristate acetate (PMA), mezerein or (−)-indolactam V. The overall effect of the protein kinase C activator is to shift the concentration-response curve of the compound to the right without affecting the maximal response;
6. The compound causes a rapid (<30 seconds) increase in the formation of inositol-1,4,5-triphosphate and/or diacylglycerol;
7. The compound inhibits dopamine- or isoproterenol-stimulated cyclic AMP formation;
8. The compound inhibits PTH secretion;
9. Pretreatment with pertussis toxin (100 ng/ml for >4 hours) blocks the inhibitory effect of the compound on cyclic AMP formation, but does not effect increases in $[Ca^{2+}]_i$, inositol-1,4,5-triphosphate, or diacylglycerol, nor decreases in PTH secretion;
10. The compound elicits increases in $Cl^-$ current in Xenopus oocytes injected with poly(A)$^+$-enriched mRNA from bovine or human parathyroid cells, but is without effect in Xenopus oocytes injected with water, or liver mRNA; and
11. Similarly, using a cloned calcium receptor from a parathyroid cell, the compound will elicit a response in Xenopus oocytes injected with the specific cDNA or mRNA encoding the receptor.

Different calcium activities can be measured using available techniques. Parallel definitions of compounds mimicking $Ca^{2+}$ activity on other calcium responsive cell, preferably at a calcium receptor, are evident from the examples provided herein and Nemeth et al., PCT/US93/01642, International Publication Number WO 94/18959.

Preferably, the compound as measured by the bioassays described herein, or by Nemeth et al., PCT/US93/01642, International Publication Number WO 94/18959, has one or more, more preferably all of the following activities: evokes a transient increase in internal calcium, having a duration of less that 30 seconds (preferably by mobilizing internal calcium); evokes a rapid increase in $[Ca^{2+}]_i$, occurring within thirty seconds; evokes a sustained increase (greater than thirty seconds) in $[Ca^{2+}]_i$ (preferably by causing an influx of external calcium); evokes an increase in inositol-1,4,5-triphosphate or diacylglycerol levels, preferably within less than 60 seconds; and inhibits dopamine- or isoproterenol-stimulated cyclic AMP formation.

The transient increase in $[Ca^{2+}]_i$ is preferably abolished by pretreatment of the cell for ten minutes with 10 mM sodium fluoride, or the transient increase is diminished by brief pretreatment (not more than ten minutes) of the cell with an activator of protein kinase C, preferably, phorbol myristate acetate (PMA), mezerein or (−) indolactam V.

B. Calcilytics

The ability of a compound to block the activity of extracellular calcium at a calcium receptor can be determined using standard techniques based on the present disclosure. (See, also Nemeth et al., PCT/US93/01642, International Publication Number WO 94/18959.) For example, compounds which block the effect of extracellular calcium, when used in reference to a parathyroid cell, possess one or more, and preferably all of the following characteristics when tested on parathyroid cells in vitro:

1. The compound blocks, either partially or completely, the ability of increased concentrations of extracellular $Ca^{2+}$ to:
   (a) increase $[Ca^{2+}]_i$,
   (b) mobilize intracellular $Ca^{2+}$,
   (c) increase the formation of inositol-1,4,5-triphosphate, (d) decrease dopamine- or isoproterenol-stimulated cyclic AMP formation, and (e) inhibit PTH secretion;

2. The compound blocks increases in $Cl^-$ current in Xenopus oocytes injected with poly(A)$^+$-mRNA from bovine or human parathyroid cells elicited by extracellular $Ca^{2+}$ or calcimimetic compounds, but not in Xenopus oocytes injected with water or liver mRNA;

3. Similarly, using a cloned calcium receptor from a parathyroid cell, the compound will block a response in Xenopus oocytes injected with the specific cDNA, mRNA or cRNA encoding the calcium receptor, elicited by extracellular $Ca^{2+}$ or a calcimimetic compound.

Parallel definitions of compounds blocking $Ca^{2+}$ activity on a calcium responsive cell, preferably at a calcium receptor, are evident from the examples provided herein and Nemeth et al., PCT/US93/01642, International Publication Number WO 94/18959.

III. Treatment of Diseases or Disorders

Diseases or disorders which can be treated using compounds able to modulate inorganic ion receptor activity include one or more of the following types: (1) those characterized by abnormal inorganic ion homeostasis, preferably calcium homeostasis; (2) those characterized by an abnormal amount of an extracellular or intracellular messenger whose production can be affected by inorganic ion receptor activity, preferably calcium receptor activity; (3) those characterized by an abnormal effect (e.g., a different effect in kind or magnitude) of an intracellular or extracellular messenger which can itself be ameliorated by inorganic ion receptor activity, preferably calcium receptor activity; and (4) other diseases or disorders in which modulation of inorganic ion receptor activity, preferably calcium receptor activity, will exert a beneficial effect, for example, in diseases or disorders where the production of an intracellular or extracellular messenger stimulated by receptor activity compensates for an abnormal amount of a different messenger. Examples of extracellular messengers whose secretion and/or effect can be affected by modulating inorganic ion receptor activity include inorganic ions, hormones, neurotransmitters, growth factors, and chemokines. Examples of intracellular messengers include cAMP, cGMP, $IP_3$, and diacylglycerol.

In a preferred embodiment, the compound is used to treat a disease or disorder characterized by abnormal bone and mineral homeostasis, more preferably calcium homeostasis. Extracellular $Ca^{2+}$ is under tight homeostatic control and controls various processes such as blood clotting, nerve and muscle excitability, and proper bone formation. Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; (5) an abnormal increase or decrease in the production and/or release of messengers which affect serum calcium levels such as parathyroid hormone and calcitonin; and (6) an abnormal change in the response elicited by messengers which affect serum calcium levels. The abnormal increase or decrease in these different aspects of calcium homeostasis is relative to that occurring in the general population and is generally associated with a disease or disorder.

Diseases and disorders characterized by abnormal calcium homeostasis can be due to different cellular defects such as a defective calcium receptor activity, a defective number of calcium receptors, or a defective intracellular protein acted on by a calcium receptor. For example, in parathyroid cells, the calcium receptor is coupled to the $G_i$ protein which in turn inhibits cyclic AMP production. Defects in $G_i$ protein can affect its ability to inhibit cyclic AMP production.

Diseases or disorders which can be treated by modulating calcium receptor activity are known in the art. For example, diseases or disorders which can be treated by modulating calcium receptor activity can be identified based on the functional responses of cells regulated by calcium receptor activity.

Functional responses of cells regulated by calcium receptor are know in the art, including PTH secretion by parathyroid cells, calcitonin secretion by C-cells, and bone resorption by osteoclasts. Such functional responses are associated with different diseases or disorders. For example, hyperparathyroidism results in elevated levels of PTH in the plasma. Decreasing the plasma levels of PTH offers an effective means of treating hyperparathyroidism. Likewise, increasing plasma levels of calcitonin is associated with an inhibition of bone resorption. Inhibiting bone resorption is an effective treatment for osteoporosis. Thus, modulation of calcium receptor activity can be used to treat diseases such as hyperparathyroidism, and osteoporosis.

Those compounds modulating inorganic ion receptor activity, preferably calcium receptor activity, can be used to confer beneficial effects to patients suffering from a variety of diseases or disorders. For example, osteoporosis is an age-related disorder characterized by loss of bone mass and increased risk of bone fracture. Compounds can be used to block osteoclastic bone resorption either directly (e.g., an osteoclast ionomimetic compound) or indirectly by increasing endogenous calcitonin levels (e.g., a C-cell calcimimetic). Alternatively, a calcilytic active on the parathyroid cell calcium receptor will increase circulating levels of parathyroid hormone, stimulating bone formation. All three of these approaches will result in beneficial effects to patients suffering from osteoporosis.

In addition, it is known that intermittent low dosing with PTH results in an anabolic effect on bone mass and appropriate bone remodeling. Thus, compounds and dosing regimens evoking transient increases in parathyroid hormone (e.g., intermittent dosing with a parathyroid cell ionolytic) can increase bone mass in patients suffering from osteoporosis.

Additional diseases or disorders can be identified by identifying additional cellular functional responses, associated with a disease or disorder, which are regulated by calcium receptor activity. Diseases or disorder which can be treated by modulating other inorganic ion receptors can be identified in an analogous manner.

Different diseases can be treated by the present invention by targeting cells having a calcium receptor. For example, primary hyperparathyroidism (HPT) is characterized by hypercalcemia and abnormal elevated levels of circulating PTH. A defect associated with the major type of HPT is a diminished sensitivity of parathyroid cells to negative feedback regulation by extracellular $Ca^{2+}$. Thus, in tissue from patients with primary HPT, the "set-point" for extracellular $Ca^{2+}$ is shifted to the right so that higher than normal concentrations of extracellular $Ca^{2+}$ are required to depress PTH secretion. Moreover, in primary HPT, even high concentrations of extracellular $Ca^{2+}$ often depress PTH secretion only partially. In secondary (uremic) HPT, a similar increase in the set-point for extracellular $Ca^{2+}$ is observed even though the degree to which $Ca^{2+}$ suppresses PTH secretion is normal. The changes in PTH secretion are paralleled by changes in $[Ca^{2+}]_i$: the set-point for extracellular $Ca^{2+}$-induced increases in $[Ca^{2+}]_i$ is shifted to the right and the magnitude of such increases is reduced.

Patients suffering from secondary HPT may also have renal osteodystrophy. Calcimimetics appear to be useful for treating both abnormal PTH secretion and renal osteodystrophy in such patients.

Compounds that mimic the action of extracellular $Ca^{2+}$ are beneficial in the long-term management of both primary and secondary HPT. Such compounds provide the added impetus required to suppress PTH secretion which the hypercalcemic condition alone cannot achieve and, thereby, help to relieve the hypercalcemic condition. Compounds with greater efficacy than extracellular $Ca^{2+}$ may overcome the apparent nonsuppressible component of PTH secretion which is particularly troublesome in the major form of primary HPT caused by adenoma of the parathyroid gland. Alternatively, or additionally, such compounds can depress synthesis of PTH, as prolonged hypercalcemia has been shown to depress the levels of preproPTH mRNA in bovine and human adenomatous parathyroid tissue. Prolonged hypercalcemia also depresses parathyroid cell proliferation in vitro, so calcimimetics can also be effective in limiting the parathyroid cell hyperplasia characteristic of secondary HPT.

Cells other than parathyroid cells can respond directly to physiological changes in the concentration of extracellular $Ca^{2+}$. For example, calcitonin secretion from parafollicular cells in the thyroid (C-cells) is regulated by changes in the concentration of extracellular $Ca^{2+}$ Isolated osteoclasts respond to increases in the concentration of extracellular $Ca^{2+}$ with corresponding increases in $[Ca^{2+}]_i$ that arise partly from the mobilization of intracellular $Ca^{2+}$. Increases in $[Ca^{2+}]_i$ in osteoclasts are associated with the inhibition of bone resorption. Release of alkaline phosphatase from bone-forming osteoblasts is directly stimulated by calcium.

Renin secretion from juxtaglomerular cells in the kidney, like PTH secretion, is depressed by increased concentrations of extracellular $Ca^{2+}$. Extracellular $Ca^{2+}$ causes the mobilization of intracellular $Ca^{2+}$ in these cells. Other kidney cells respond to calcium as follows: elevated $Ca^{2+}$ inhibits formation of $1,25(OH)_2$-vitamin D by proximal tubule cells, stimulates production of calcium-binding protein in distal tubule cells, and inhibits tubular reabsorption of $Ca^{2+}$ and $Mg^{2+}$ and the action of vasopressin on the thick ascending limb of Henle's loop (MTAL), reduces vasopressin action in the cortical collecting duct cells, and affects vascular smooth muscle cells in blood vessels of the renal glomerulus.

Calcium also promotes the differentiation of intestinal goblet cells, mammary cells, and skin cells; inhibits atrial natriuretic peptide secretion from cardiac atria; reduces cAMP accumulation in platelets; alters gastrin and glucagon secretion; acts on vascular smooth muscle cells to modify cell secretion of vasoactive factors; and affects cells of the central nervous system and peripheral nervous system.

Thus, there are sufficient indications to suggest that $Ca^{2+}$, in addition to its ubiquitous role as an intracellular signal, also functions as an extracellular signal to regulate the responses of certain specialized cells. Compounds of this invention can be used in the treatment of diseases or disorders associated with disrupted $Ca^{2+}$ responses in these cells.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea, and spastic colon; GI ulcer diseases; GI diseases with excessive calcium absorption such as sarcoidosis; and autoimmune diseases and organ transplant rejection.

While calcium receptor-modulating compounds of the present invention will typically be used in therapy for human patients, they may also be used to treat similar or identical diseases in other warm-blooded animal species such as other primates, farm animals such as swine, cattle, and poultry; and sports animals and pets such as horses, dogs and cats.

IV. Administration

The compounds described by the present invention can be formulated for a variety of modes of administration, including systemic and topical or localized administration. Techniques and formulations generally may be found in *Remington's Pharmaceutical Sciences,* $18^{th}$ ed., Mack Publishing Co., Easton, Pa., 1990 (hereby incorporated by reference herein).

Suitable dosage forms, in part, depend upon the use or the route of entry, for example, oral, transdermal, transmucosal, or by injection (parenteral). Such dosage forms should allow the compound to reach a target cell whether the target cell is present in a multicellular host or in culture. For example, pharmacological compounds or compositions injected into the blood stream should be soluble. Other factors are known in the art, and include considerations such as toxicity and dosage forms which retard the compound or composition from exerting its effect.

Compounds can also be formulated as pharmaceutically acceptable salts and complexes thereof. Pharmaceutically acceptable salts are non-toxic salts in the amounts and concentrations at which they are administered. The preparation of such salts can facilitate the pharmacological use by altering the physical characteristics of the compound without preventing it from exerting its physiological effect. Useful alterations in physical properties include lowering the melting point to facilitate transmucosal administration and increasing the solubility to facilitate administering higher concentrations of the drug.

The pharmaceutically acceptable salt of the different compounds may be present as a complex. Examples of complexes include an 8-chlorotheophylline complex (analogous to, e.g., dimenhydrinate:diphenhydramine 8-chlorotheophylline (1:1) complex; Dramamine) and various cyclodextrin inclusion complexes.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol, are present. For example, see *Remington's Pharmaceutical Sciences*, 18th ed., Mack Publishing Co., Easton, Pa., p. 1445, 1990. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent. (See, e.g., PCT/US92/03736, hereby incorporated by reference herein.)

Carriers or excipients can also be used to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution and dextrose.

The compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, for example, intramuscular, intravenous, intraperitoneal, and/or subcutaneous administration. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, buccal or sublingual tablets, rectal suppositories, or vaginal suppositories.

For topical administration, the compounds of the invention can be formulated into ointments, salves, gels, or creams, as is generally known in the art.

The amounts of various compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art. Generally, it is an amount between about 0.01 and 50 mg/kg, preferably 0.01 and 20 mg/kg of the animal to be treated.

V. EXAMPLES

Examples are provided below illustrating different aspects and embodiments of the present invention. These examples are not intended to limit the claimed invention. Included in these examples are synthesis protocols illustrating techniques which can be used to synthesize different compounds described herein. Other compounds falling within the generic groups described herein can be prepared using standard techniques.

Example 1

Assaying Calcium Receptor Activity

The ability of different compounds to modulate calcium receptor activity are described in this example. Other methods which can be used to measure calcium receptor activity are known in the art.

Recombinant HEK 293 4.0–7 cells containing a calcium receptor were constructed as described by Rogers et al., *J. Bone Miner. Res.* 10 Suppl. 1:S483, 1995 (hereby incorporated by reference herein). The recombinant cells were loaded with fura-2 by incubating the cells in Dulbecco's modified Eagle's medium buffered with 20 mM HEPES containing about 5 $\mu$M fluo-3/AM for one hour at room temperature. Cells were then rinsed with Hank's balanced salt solution buffered with 20 mM HEPES containing 1 mM $CaCl_2$ and 1 mM $MgCl_2$. Compounds to be tested were then added to the cells and fluorescence was measured (excitation and emission wavelengths of 340 and 510 nm, respectively). Table I provides results for different compounds.

TABLE I

| Compound | $EC_{50}$ (nM) |
| --- | --- |
| 26A | 52(1) |
| 6X | 286 |
| 26B | 10900 |
| 26C | 22000 |
| 26D | 47(3) |
| 26E | 77(3) |
| 26F | 15(3) |
| 26G | 11(3) |
| 26H | 36(1) |
| 26I | 126(1) |
| 26J | 47(1) |
| 27E | 12000 |
| 27F | 230 |
| 27G | 70 |
| 27H | 2750 |
| 28O | 2500 |
| 27J | 1100 |
| 27K | 3800 |
| 27L | >100000 |
| 27M | 1800 |
| 27N | 960 |
| 27O | 29 |
| 27P | 1600 |
| 27Q | 23 |
| 27R | 2550 |
| 27S | 210 |

TABLE I-continued

| Compound | EC$_{50}$ (nM) |
|---|---|
| 27T | 2900 |
| 27U | 210 |
| 27V | 140 |
| 27W | 1500 |
| 27X | 22 |
| 27Y | 12 |
| 27Z | 16 |
| 28A | 9.5 |
| 28B | 24 |
| 28C | 270 |
| 28D | 7300 |
| 28E | 810 |
| 28F | 660 |
| 28G | 602 |
| 28H | 3000 |
| 28I | 1200 |
| 28J | 1100 |
| 28K | 57 |
| 28L | >3000 |
| 28M | 170 |
| 28N | 303 |

Example 2

Synthesis of 26D, (R,R)-N-(1-Ethyl-4'-iodophenyl)-1-(1-naphthyl)ethylamine hydrochloride The synthesis of the title compound (26D) was accomplished in a one-pot, two-step reaction sequence by reductive amination of the imine formed from the commercially available 4'-iodoacetophenone and (R)-naphthyl-1-ethylamine. The reduction of the imine diastereoselectively was conducted under similar conditions as previously reported (*Tetrahedron Lett.* (1985) 41, 6005–6011.).

A mixture of 4'-iodoacetophenone (0.25 g, 1.0 mmol), (R)-naphthyl-1-ethylamine (0.17 g, 1.0 mmol), and Ti(i-PrO)$_4$ (0.38 mL, 1.1 mmol) in abs. EtOH (5 mL) was refluxed for 18 h. Diethyl-1,4-dihydro-2,6-dimethyl-3,5-pyridine decarboxylate (0.25 g, 1.0 mmol) and Mg(ClO$_4$)$_2$ (0.22 g, 1.0 mmol) were then added to the reaction mixture and the reflux was continued for an additional 18 h. The reaction mixture was then cooled to ambient temperature, H$_2$O (3 mL) and diethyl ether (10 mL) were added and the mixture was centrifuged (3000 rpm) to remove the inorganic salts. The supernatant was decanted away from the pellet and the volatiles were removed under reduced pressure. The resulting residue was chromatographed on silica gel (elution with 1% MeOH/CH$_2$Cl$_2$) to provide the purified product as its free base. This material was converted to its hydrochloride salt. The salt was recrystallized from CH$_2$Cl$_2$/hexane to provide GC/MS-pure material.

Example 3

Synthesis of 26E, (R,R)-N-(1-Ethyl-4'-ethoxy-3'-methylphenyl)-1-(1-naphthyl)ethylamine hydrochloride The synthesis of the title compound (26E) was accomplished in a three-step, two-pot reaction sequence. Commercially available 4-hydroxy-3-methylacetophenone was O-alkylated with ethyl iodide/K$_2$CO$_3$/acetone. This ketone was subsequently reacted with (R)-naphthyl-1-ethylamine in the presence of Ti(i-PrO)$_4$ to provide the imine. This imine was reduced in high diastereoselective yield by catalytic hydrogenation with Raney-nickel.

A mixture of 4-ethoxy-3-methylacetophenone (2.0 g, 11.2 mmol), (R)-naphthyl-1-ethylamine (2.0 g, 11.2 mmol), Ti(i-Pro)$_4$ (4.2 mL, 14.1 mmol), and EtOH (10 mL) were stirred at 60° C. for 18 h. The reaction mixture was then transferred to a Parr hydrogenation flask, Raney-nickel (100 mg; washed with EtOH, 3×20 mL) was added, and the mixture was hydrogenated at 50 psig, 25° C., for 4 h. The reaction mixture was then filtered (Celite/fritted glass), the catalyst was washed (EtOH, 20 mL), and the filtrate was evaporated under reduced pressure to provide the crude product. This material was purified by silica gel chromatography (elution with 2% MeOH/CH$_2$Cl$_2$). The free base was converted to its hydrochloride salt to provide 1.1 g (27%) of a white solid.

Example 4

Synthesis of 26F, (R,R)-N-(1-Propyl-4'-methoxy-3'-methylphenyl)-1-(1-naphthyl)ethylamine hydrochloride The synthesis of the title compound (26F) was accomplished in a four-step, three-pot reaction sequence. Commercially available 3-methyl-p-anisaldehyde was reacted with ethylmagnesium bromide to provide its phenylpropanol derivative. This alcohol was then oxidized to the corresponding ketone in the usual manner with PCC. This ketone was subsequently reacted with (R)-naphthyl-1-ethylamine in the presence of Ti(i-PrO)$_4$ to provide the imine. This imine was reduced in high diastereoselective yield by catalytic hydrogenation in the presence of Raney-nickel.

In a manner similar to the synthesis of 26E, a mixture of 4-methoxy-3-methylpropiophenone (5.7 g, 31.7 mmol), (R)-naphthyl-1-ethylamine (5.2 mL, 31.7 mmol), Ti(i-Pro)$_4$ (11.8 mL, 39.6 mmol), and EtOH (30 mL) were reacted as above to form the imine which was subsequently reduced under catalytic hydrogenation conditions over Raney-nickel. The crude product was purified by silica gel chromatography (elution with 10:1, hexane/EtOAc). The free base was converted to its hydrochloride salt to provide 0.50 g (4%) of a white solid.

Example 5

Synthesis of 26G, (R,R)-N-(1-Ethyl-4'-methoxy-3'-bromophenyl)-1-(1-naphthyl)ethylamine hydrochloride The synthesis of the title compound (26G) was accomplished in a four-step, three-pot reaction sequence. Commercially available 3-bromo-4-methoxybenzaldehyde was reacted with methylmagnesium bromide to provide its phenylethanol derivative. This alcohol was then oxidized to the corresponding ketone in the usual manner with pyridinium chlorochromate (PCC). This ketone was subsequently reacted with (R)-naphthyl-1-ethylamine in the presence of Ti(i-PrO)$_4$ to provide the imine. This imine was reduced in high diastereoselective yield using diethyl-1,4-dihydro-2,6-dimethyl-3,5-pyridine decarboxylate.

In a manner similar to the synthesis of 26D, a mixture of 3-bromo-4-methoxyacetophenone (3.0 g, 13.1 mmol), (R)-naphthyl-1-ethylamine (2.1 mL, 13.1 mmol), and Ti(i-PrO)$_4$ (4.7 mL, 15.7 mmol) in abs. EtOH (100 mL) was reduced with diethyl-1,4-dihydro-2,6-dimethyl-3,5-pyridine decarboxylate in the presence of Mg(ClO$_4$)$_2$. The resulting crude material was converted to its hydrochloride salt. The salt was purified by precipitation from diethyl ether/hexane to provide GC/MS-pure material (0.6 g, 11%) as a white solid.

Example 6

Synthesis of 26H, 26I, and 26J, (R)-N-(3-phenyl-2-propenyl)-1-(1-naphthyl)ethylamine hydrochloride, (R)-N-(2-methyl-3-phenyl-2-propenyl)-1-(1-naphthyl)ethylamine hydrochloride, and (R)-N-(2-methoxy-3-phenyl-2-propenyl)-1-(1-naphthyl)ethylamine hydrochloride The syntheses of the title compounds were accomplished in three, two-step, one-pot reaction sequences. Commercially available cinnamaldehyde, 2-methyl-trans-cinnamaldehyde, and 2-methoxycinnamaldehyde, respectively, were reacted with (R)-naphthyl-1-ethylamine in the presence of Ti(i-Pro)$_4$ to provide the corresponding imine. These imines were reduced using sodium cyanoborohydride to provide the title compounds in high overall yields.

Example 7

Physical Data

Table II provides physical data for some of the compounds described herein. Gas chromatographic and mass spectral data were obtained on a Hewlett-Packard 5890 Series II Gas Chromatograph with a 5971 Series Mass Selective Detector [Ultra-2 Ultra Performance Capillary Column (crosslinked 5% Ph Me silicone); column length, 25 m, column i.d., 0.20 mm, film thickness, 0.33 µm; He flow rate, 60 mL/min; injector temp., 250° C.; temp. program, 20° C./min from 125 to 325° C. for 10 min, then held constant at 325° C. for 6 min].

TABLE II

| Compound | GC$_{rt}$ | m/z |
|---|---|---|
| 25Z | 8.32 | 285 |
| 26A | 8.75 | 286 |
| 26B | 8.51 | 288 |
| 26C | 9.60 | 346 |
| 26D | 11.08 | 401 |
| 26E | 10.71 | 333 |
| 26F | 10.56 | 333 |
| 26G | 9.09 | 385 |
| 26H | 10.95 | 287 |
| 26I | 10.98 | 301 |
| 26J | 11.79 | 317 |

Additional Gas chromatographic and mass spectral data were obtained on a Hewlett-Packard 5890 Series II Gas Chromatograph with a 5971 Series Mass Selective Detector [Ultra-2 Ultra Performance Capillary Column (crosslinked 5% phenyl methyl silicone); column length, 25 m, column i.d., 0.20 mm; He flow rate, 60 mL/min; injector temp., 250° C.; gradient temperature program, 20° C./min from 125 to 325° C. for 10 min, then held constant at 325° C. for 6 min].

Compound 26Z, rt=10.22', m/z (rel. int.) 331 (M+,15), 316 (56), 182 (9), 168 (5), 156 (20), 155 (100), 154 (28), 153 (18), 152 (8), 141 (11), 133 (43), 131 (5), 129 (11), 128 (18), 127 (15), 117 (9), 115 (13), 115 (13), 105 (8), 91 (7).

Compound 27A, rt=10.13', m/z (rel. int.) 331 (M+,18), 316 (76), 182 (10), 176 (5), 168 (10), 167 (5), 156 (17), 155 (100), 154 (57), 153 (27), 152 (14), 141 (14), 134 (7), 133 (58), 133 (58), 131 (7), 129 (14), 128 (21), 127 (23), 126 (5), 119 (5), 117 (12), 116 (5), 115 (18), 105 (10), 91 (12), 77 (5), Compound 27D, rt=9.41', m/z (rel. int.) 292 (M+,5), 171 (7), 160 (7), 157 (9), 147 (6), 146 (9), 145 (66), 143 (7), 134 (7), 133 (20), 132 (11), 131 (13), 129 (10), 119 (11), 117 (25), 116 (100), 115 (14), 115 (14), 105 (10), 103 (5), 91 (16), 89 (17), 77 (8).

Compound 27E, rt=7.81', m/z (rel. int.) 283 (M+,3), 268 (100), 176 (16), 150 (14), 149 (39), 148 (7), 135 (7), 134 (11), 121 (19), 118 (6), 117 (6), 115 (6), 109 (10), 105 (8), 104 (11), 103 (9), 92 (12), 91 (75), 79 (9), 78 (10), 77 (21), 77 (21), 65 (15), 51 (5), 42 (6), 41 (6).

Compound 27F, rt=7.38', m/z (rel. int.) 365 (M+,1), 231 (6), 230 (31), 216 (28), 215 (59), 214 (17), 190 (15), 174 (25), 136 (41), 135 (100), 134 (14), 129 (13), 128 (15), 127 (9), 119 (9), 117 (6), 114 (9), 109 (10), 105 (21), 104 (7), 103 (18), 91 (21), 91 (10), 79 (11), 78 (7), 77 (19), 68 (12), 65 (6), 42 (9), 0 (0).

Compound 27G, rt=7.45', m/z (rel. int.) 365 (M+,4), 231 (8), 230 (49), 216 (44), 215 (86), 213 (27), 190 (23), 187 (6), 175 (6), 174 (31), 136 (37), 135 (100), 134 (14), 130 (8), 129 (11), 128 (13), 127 (9), 120 (7), 120 (7), 116 (5), 115 (8), 109 (8), 105 (19), 103 (13), 92 (8), 91 (16), 79 (8), 77 (13), 68 (9), 0 (0).

Compound 27H, rt=10.44', m/z (rel. int.) 317 (M+,8), 170 (9), 162 (5), 155 (19), 154 (28), 153 (14), 152 (9), 148 (5), 147 (13), 146 (100), 134 (7), 129 (6), 128 (18), 127 (21), 126 (7), 115 (12), 115 (12), 103 (7), 102 (6), 89 (8), 77 (8).

Compound 27J, rt=9.88', m/z (rel. int.) 337 (M+,2), 323 (22), 322 (100), 210 (26), 196 (9), 184 (12), 182 (11), 170 (13), 169 (53), 168 (31), 167 (14), 165 (10), 154 (22), 153 (41), 152 (32), 150 (9), 141 (53), 129 (27), 128 (34), 127 (62), 126 (20), 124 (98), 115 (24), 103 (23), 91 (15), 89 (18), 77 (23), 42 (11), 41 (9), 0 (0).

Compound 27K, rt=9.03', m/z (rel. int.) 342 (M+,0.1), 327 (40), 325 (41), 308 (14), 306 (21), 204 (17), 202 (31), 174 (43), 173 (26), 172 (66), 171 (26), 139 (11), 138 (15), 137 (20), 127 (33), 124 (100), 117 (10), 115 (12), 111 (11), 103 (37), 102 (41), 101 (30), 98 (12), 91 (11), 89 (28), 77 (35), 75 (21), 63 (12), 51 (10), 0 (0).

Compound 27L, rt=8.84', m/z (rel. int.) 264 (M+,24), 145 (100), 145 (7), 119 (29), 118 (26), 118 (16), 117 (7), 116 (5), 102 (37), 92 (10), 91 (41), 90 (41), 77 (6), 76 (9), 75 (14), 75 (14), 65 (S), 64 (21), 63 (23), 51 (8).

Compound 27M, rt=8.48', m/z (rel. int.) 305 (M+,0.0), 291 (6), 290 (31), 164 (28), 136 (17), 135 (100), 120 (6), 111 (7), 111 (7), 105 (16), 103 (9), 98 (7), 92 (6), 91 (13), 79 (8), 77 (12), 65 (5), 63 (5).

Compound 27N, rt=8.81', m/z (rel. int.) 294 (M+,6), 279 (100), 187 (5), 164 (7), 144 (7), 136 (16), 135 (75), 135 (75), 134 (11), 130 (15), 121 (6), 120 (7), 117 (11), 116 (36), 115 (6), 105 (18), 104 (14), 103 (30), 102 (7), 92 (9), 91 (19), 90 (6), 89 (17), 79 (10), 78 (7), 77 (23), 65 (6), 63 (6).

Compound 27O, rt=9.33', m/z (rel. int.) 347 (M+,1), 304 (58), 192 (6), 156 (14), 156 (14), 155 (100), 154 (22), 153 (22), 152 (9), 150 (24), 149 (16), 148 (23), 135 (28), 129 (9), 128 (14), 127 (15), 115 (9), 91 (8), 77 (6).

Compound 27P, rt=9.23', m/z (rel. int.) 347 (M+,0.0), 304 (100), 177 (3), 156 (12), 155 (87), 154 (12), 153 (15), 152 (6), 150 (20), 149 (10), 148 (12), 128 (6), 127 (6).

Compound 27Q, rt=9.64', m/z (rel. int.) 361 (M+,0.1), 304 (54), 156 (17), 155 (100), 153 (17), 152 (7), 151 (5), 150 (40), 148 (12), 135 (27), 129 (7), 128 (9), 127 (9), 115 (7), 91 (5), 91 (5).

Compound 27R, rt=9.16', m/z (rel. int.) 294 (M+,3), 279 (100), 187 (5), 164 (6), 136 (24), 135 (77), 121 (10), 120 (6), 117 (5), 116 (33), 105 (15), 104 (7), 103 (15), 92 (6), 91 (14), 91 (14), 89 (10), 79 (8), 78 (5), 77 (14), 65 (5).

Compound 27S, rt=9.27', m/z (rel. int.) 338 (M+,0.0), 323 (7), 322 (38), 164 (9), 162 (7), 160 (25), 158 (37), 136 (25), 136 (6), 135 (100), 134 (16), 124 (7), 122 (6), 120 (8), 120 (7), 115 (8), 105 (19), 104 (5), 103 (16), 102 (11), 101 (9), 92 (10), 91 (19), 89 (8), 79 (10), 78 (6), 77 (17), 65 (6), 63 (6), 0 (0).

Compound 27U, rt=8.65', m/z (rel. int.) 385 (M+,3), 230 (16), 230 (16), 216 (12), 215 (55), 214 (15), 210 (12), 174 (19), 156 (23), 155 (100), 154 (27), 153 (24), 152 (12), 140 (5), 129 (15), 128 (25), 127 (22), 126 (5), 115 (12), 109 (5), 68 (5).

Compound 27V, rt=8.59', m/z (rel. int.) 385 (M+,3), 230 (14), 216 (9), 215 (49), 214 (13), 210 (5), 174 (17), 156 (23), 155 (100), 154 (25), 153 (26), 152 (11), 130 (5), 129 (19), 129 (19), 128 (27), 127 (26), 115 (14), 109 (6), 101 (5), 77 (5), 69 (7).

Compound 27W, rt=8.88', m/z (rel. int.) 371 (M+,2), 356 (100), 244 (20), 184 (5), 182 (5), 170 (8), 169 (24), 168 (14), 167 (8), 160 (5), 159 (46), 154 (11), 153 (24), 153 (24), 152 (15), 150 (6), 141 (26), 133 (9), 129 (11), 128 (13), 127 (19), 126 (5), 115 (6), 109 (10).

Compound 27x, rt=10.61', m/z (rel. int.) 419 (M+,0.0), 406 (50), 404 (20), 403 (100), 402 (11), 401 (51), 263 (6), 250 (27), 248 (55), 246 (29), 169 (9), 167 (7), 156 (5), 155 (14), 154 (16), 153 (12), 153 (12), 152 (6), 128 (9), 127 (9).

Compound 27Y, rt=10.21', m/z (rel. int.) 375 (M+,4), 361 (20), 360 (100), 359 (15), 358 (78), 279 (7), 217 (11), 206 (23), 205 (7), 204 (93), 202 (74), 170 (13), 168 (8), 156 (12), 155 (38), 154 (53), 153 (37), 152 (21), 141 (11), 129 (16), 128 (37), 127 (41), 126 (21), 123 (20), 115 (14), 89 (28), 77 (10), 75 (10), 63 (8), 0 (0).

Compound 27Z, rt=11.10', m/z (rel. int.) 466 (M+,0.1), 451 (60), 450 (13), 449 (61), 311 (9), 309 (11), 296 (97), 295 (8), 294 (100), 169 (29), 168 (9), 167 (24), 156 (20), 155 (56), 154 (74), 153 (45), 152 (27), 151 (8), 141 (13), 129 (21), 128 (52), 127 (61), 126 (18), 115 (18), 89 (43), 77 (13), 75 (14), 74 (9), 63 (16), 0 (0).

Compound 28A, rt=10.73', m/z (rel. int.) 421 (M+,4), 408 (33), 407 (21), 407 (21), 406 (100), 279 (9), 265 (7), 252 (22), 251 (6), 250 (70), 156 (6), 155 (20), 154 (25), 153 (19), 152 (11), 141 (6), 129 (7), 128 (18), 127 (21), 126 (10), 123 (11), 115 (7), 89 (16).

Compound 28B, rt=10.75', m/z (rel. int.) 417 (M+,3), 274 (5), 261 (16), 261 (16), 247 (10), 246 (100), 156 (7), 155 (29), 154 (35), 153 (19), 152 (11), 141 (6), 129 (8), 128 (23), 127 (23), 126 (7), 115 (8), 105 (9), 91 (7), 90 (16), 89 (9), 77 (15).

Compound 28C, rt=8.73', m/z (rel. int.) 317 (M+,0.1), 303 (12), 302 (62), 282 (9), 178 (6), 149 (22), 148 (100), 148 (7), 135 (9), 131 (6), 127 (16), 124 (46), 119 (12), 117 (6), 115 (8), 104 (6), 103 (24), 102 (6), 92 (9), 91 (65), 90 (7), 89 (18), 78 (6), 77 (25), 65 (19), 63 (11).

Compound 28D, rt=8.73', m/z (rel. int.) 317 (M+,0.1), 303 (14), 302 (71), 282 (11), 178 (6), 149 (23), 149 (23), 148 (100), 135 (9), 131 (6), 127 (14), 124 (42), 119 (10), 117 (5), 115 (7), 103 (19), 92 (8), 91 (56), 90 (5), 89 (14), 78 (6), 77 (19), 65 (16), 63 (7).

Compound 28E, rt=9.33', m/z (rel. int.) 338 (M+,2), 325 (7), 324 (35), 323 (11), 323 (11), 322 (54), 164 (9), 161 (15), 159 (23), 136 (30), 135 (100), 121 (15), 120 (5), 105 (14), 103 (10), 92 (5), 91 (11), 79 (7), 77 (11).

Compound 28F, rt=9.11', m/z (rel. int.) 338 (M+,1), 325 (7), 324 (39), 323 (11), 322 (59), 164 (10), 161 (19), 161 (19), 159 (29), 136 (27), 135 (100), 121 (11), 120 (6), 115 (5), 105 (17), 103 (12), 102 (7), 101 (5), 92 (6), 91 (14), 89 (6), 79 (9), 77 (14), 65 (5).

Compound 28G, rt=7.18', m/z (rel. int.) 251 (M+,6), 236 (43), 156 (6), 155 (26), 154 (32), 153 (24), 152 (18), 152 (18), 151 (6), 141 (8), 129 (11), 128 (25), 127 (31), 126 (11), 115 (12), 95 (12), 82 (6), 81 (100), 77 (8), 53 (27), 51 (6).

Compound 28H, rt=7.31', m/z (rel. int.) 251 (M+,9), 236 (100), 208 (7), 170 (10), 168 (8), 156 (5), 155 (26), 154 (39), 153 (27), 152 (19), 152 (19), 151 (6), 141 (8), 129 (9), 128 (22), 127 (29), 126 (10), 115 (9), 94 (5), 82 (5), 81 (77), 53 (13).

Compound 28I, rt=8.20', m/z (rel. int.) 267 (M+,6), 252 (36), 156 (6), 155 (21), 154 (15), 153 (15), 152 (10), 141 (7), 129 (7), 128 (15), 127 (16), 126 (5), 115 (8), 112 (16), 98 (8), 98 (8), 98 (6), 96 (100), 53 (5), 44 (6).

Compound 28J, rt=8.23', m/z (rel. int.) 267 (M+,6), 251 (56), 170 (11), 155 (25), 154 (31), 153 (23), 153 (23), 152 (16), 151 (5), 141 (7), 129 (9), 128 (22), 127 (26), 126 (9), 115 (10), 111 (7), 110 (7), 98 (6), 97 (8), 96 (100), 85 (5), 77 (5), 53 (6), 44 (9).

Compound 28K, rt=9.28', m/z (rel. int.) 315 (M+,42), 301 (5), 300 (23), 160 (19), 156 (19), 155 (78), 154 (42), 153 (27), 152 (15), 146 (16), 145 (100), 144 (19), 141 (6), 129 (11), 128 (24), 127 (31), 127 (31), 126 (8), 118 (7), 117 (14), 116 (8), 115 (41), 91 (12), 89 (9), 77 (7).

Compound 28L, rt=7.41', m/z (rel. int.) 319 (M+,6), 318 (8), 159 (15), 147 (12), 146 (100), 132 (6), 131 (5), 130 (7), 119 (6), 117 (13), 115 (10), 109 (8), 105 (6), 104 (16), 103 (11), 91 (8), 78 (8), 77 (8), 42 (8).

Compound 28M, rt=10.76', m/z (rel. int.) 372 (M+,2), 360 (8), 359 (10), 358 (44), 357 (16), 356 (68), 169 (6), 168 (29), 167 (8), 160 (32), 158 (51), 156 (17), 155 (100), 154 (29), 153 (34), 152 (18), 151 (6), 141 (9), 129 (18), 128 (25), 127 (28), 126 (8), 124 (7), 122 (9), 115 (19), 102 (6), 101 (7), 89 (10), 77 (7), 0 (0).

Compound 28N, rt=7.40', m/z (rel. int.) 270 (M+,6), 136 (62), 135 (100), 133 (20), 120 (12), 120 (8), 106 (5), 105 (34), 103 (18), 103 (18), 103 (6), 91 (28), 91 (23), 79 (11), 79 (5), 78 (11), 77 (22), 76 (5), 64 (10), 63 (5), 62 (7).

Other embodiments are within the following claims. Thus, while several embodiments have been shown and described, various modifications may be made without departing from the spirit and scope of the present invention.

What is claimed is:

1. A pharmaceutical composition comprising a therapeutically effective amount of a calcium receptor-modulating compound having the formula:

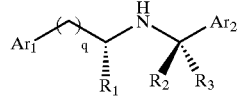

wherein $Ar_1$ is either optionally substituted naphthyl, optionally substituted phenyl, or an optionally substituted heterocyclic aryl, wherein up to S substituents may be present and each substituent is independently selected from the group consisting of: alkyl, alkenyl, halogen, alkoxy, thioalkyl, methylene dioxy, halo alkyl, haloalkoxy, OH, $CH_2OH$, $CONH_2$, CN, acetoxy, $N(alkyl)_2$, phenyl, phenoxy, benzyl, benzyloxy, α-α-dimethylbenzyl, $NO_2$, CHO, $CH_3CH(OH)$, acetyl, $OCH_2COOH$, and ethylene dioxy;

$Ar_2$ is either optionally substituted naphthyl or optionally substituted phenyl wherein up to 5 substituents may be present and each substituent is independently selected from the group consisting of: alkyl, alkenyl, halogen, alkoxy, thioalkyl, methylene dioxy, haloalkyl, halo alkoxy, OH, $CH_2OH$, $CONH_2$, CN, $OCH_2COOH$, ethylene dioxy, and acetoxy;

q is 0, 1, 2, or 3 provided that if q is 2, then $Ar_2$ is not an unsubstituted phenyl;

$R_1$ is either H or alkyl; and $R_2$ and $R_3$ are each independently either an alkyl, or together cycloalkyl or cycloalkenyl;

or a pharmaceutically acceptable salt or complex thereof; and a pharmaceutically acceptable carrier.

2. The pharmaceutical composition of claim 1, wherein $Ar_1$ is either optionally substituted phenyl or optionally substituted naphthyl.

3. The pharmaceutical composition of claim 2, wherein $R_2$ and $R_3$ are both methyl.

4. The pharmaceutical composition of claim 3, wherein $R_1$ is hydrogen.

5. The pharmaceutical composition of claim 3, wherein $Ar_2$ is a substituted phenyl.

6. The pharmaceutical composition of claim 5, wherein said $Ar_2$ substituted phenyl has one to four independently selected substituents, provided that at least one substituent is located in the meta position.

7. The pharmaceutical composition of claim 6, wherein said $Ar_2$ substituted phenyl has 1 to 4 substituents each independently selected from the group consisting of: isopropyl, $CH_3O$, $CH_3S$, $CF_3O$, Br, I, Cl, F, $CF_3$, and $CH_3$.

8. The pharmaceutical composition of claim 3, wherein $Ar_2$ is an optionally substituted naphthyl.

9. The pharmaceutical composition of claim 8, wherein $Ar_2$ is an unsubstituted naphthyl.

10. The pharmaceutical composition of claim 8, wherein $Ar_2$ is a substituted naphthyl having 1 to 4 independently selected substituents selected from the group consisting of: isopropyl, $CH_3O$, $CH_3S$, $CF_3O$, Br, I, Cl, F, $CF_3$, and $CH_3$.

11. The pharmaceutical composition of claim 1, wherein said compound is selected from the group consisting of:

N-(3-(2-chlorophenyl)propyl)-1-methyl-1-(3-methoxyphenyl)ethylamine;

N-(3-(2-chlorophenyl)propyl)-1-methyl-1-(2-methoxyphenyl)ethylamine;

N-(3-(2-chlorophenyl)propyl)-1-methyl-1-(4-methoxyphenyl)ethylamine;

N-(3-phenylpropyl)-1-methyl-1-(3-methoxyphenyl)ethylamine;

N-(3-(3-trifluoromethyl)phenyl)propyl)-1-methyl-1-(3-methoxyphenyl)ethylamine; and N-(3-(3-trifluoromethyl)phenyl)propyl)-1-methyl-1-(1-naphthyl)ethylamine;

or a pharmaceutically acceptable salt or complex thereof.

12. A method for treating a patient in need of such treatment comprising the step of administering to said patient a therapeutically effective amount of a pharmaceutical composition of any one of claims 1–11.

13. A method of treating a patient by decreasing plasma $Ca^{2+}$ comprising the step of administering to said patient an effective amount of a pharmaceutical composition of claims 1–11.

14. A method of treating a patient having a disease characterized by either, or both, of: (1) abnormal calcium homeostasis, and (2) an abnormal amount of an extracellular or intracellular messenger whose production can be affected by calcium receptor activity comprising:

administering to said patient a pharmaceutical composition comprising a therapeutically effective amount of a compound having the formula:

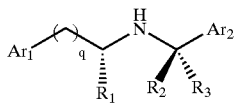

wherein $Ar_1$ is either optionally substituted naphthyl, optionally substituted phenyl, or an optionally substituted heterocyclic aryl, wherein up to 5 substituents may be present and each substituent is independently selected from the group consisting of: alkyl, alkenyl, halogen, alkoxy, thioalkyl, methylene dioxy, haloalkyl, haloalkoxy, OH, $CH_2OH$, $CONH_2$, CN, acetoxy, $N(alkyl)_2$, phenyl, phenoxy, benzyl, benzyloxy, α,α-dimethylbenzyl, $NO_2$, CHO, $CH_3CH(OH)$, acetyl, $OCH_2COOH$, and ethylene dioxy;

$Ar_2$ is either optionally substituted naphthyl, optionally substituted phenyl, or an optionally substituted heterocyclic aryl, wherein up to 5 substituents may be present and each substituent is independently selected from the group consisting of: alkyl, alkenyl, halogen, alkoxy, thioalkyl, methylene dioxy, haloalkyl, haloalkoxy, OH, $CH_2OH$, $CONH_2$, CN, $OCH_2COOH$, ethylene dioxy, and acetoxy;

q is 0, 1, 2, or 3;

$R_1$ is either H or alkyl; and $R_2$ and $R_3$ are each independently either alkyl, or together cycloalkyl or cycloalkenyl;

or a pharmaceutically acceptable salt or complex thereof; and a pharmaceutically acceptable carrier.

15. The method of claim 14, wherein $Ar_1$ is either optionally substituted phenyl or optionally substituted naphthyl.

16. The method of claim 15, wherein $R_2$ and $R_3$ are both methyl.

17. The method of claim 16, wherein $R_1$ is hydrogen.

18. The method of claim 16, wherein $Ar_2$ is a substituted phenyl.

19. The method of claim 18, wherein said $Ar_2$ substituted phenyl has one to four independently selected substituents, provided tat at least one substituent is located in the meta position.

20. The method of claim 19, wherein said $Ar_2$ substituted phenyl has 1 to 4 substituents each independently selected from the group consisting of: isopropyl, $CH_3O$, $CH_3S$, $CF_3O$, Br, I, Cl, F, $CF_3$, and $CH_3$.

21. The method of claim 16, wherein $Ar_2$ is an optionally substituted naphthyl.

22. The method of claim 21, wherein $Ar_2$ is an unsubstituted naphthyl.

23. The method of claim 21, wherein $Ar_2$ is a substituted naphthyl having 1 to 4 independently selected substituents selected from the group consisting of: isopropyl, $CH_3O$, $CH_3S$, $CF_3O$, Br, I, Cl, F, $CF_3$, and $CH_3$.

24. The method of claim 18, wherein said pharmaceutical composition contains a compound selected from the group consisting of:

N-(3-(2-chlorophenyl)propyl)-1-methyl-1-(3-methoxyphenyl)ethylamine;

N-(3-(2-chlorophenyl)propyl)-1-methyl-1-(2-methoxyphenyl)ethylamine;

N-(3-(2-chlorophenyl)propyl)-1-methyl-1-(4-methoxyphenyl)ethylamine;

N-(3-phenylpropyl)-1-methyl-1-(3-methoxyphenyl)ethylamine;

N-(3-(3-trifluoromethyl)phenyl)propyl)-1-methyl-1-(3-methoxyphenyl)ethylamine; and N-(3-(3-trifluoromethyl)phenyl)propyl)-1-methyl-(1-naphthyl)ethylamine;

or a pharmaceutically acceptable salt or complex thereof.

25. The method of any one of claims 14–24, wherein said patient has a disease selected from the group consisting of: primary or secondary hyperparathyroidism, Paget's disease, hypercalcemia malignancy, osteoporosis, hypertension, and renal osteodystrophy.

26. The method of claim 25, wherein said disease is primary or secondary hyperparathyroidism.

* * * * *

UNITED STATES PATENT AND TRADEMARK OFFICE
CERTIFICATE OF CORRECTION

PATENT NO. : 6,710,088 B2
DATED : March 23, 2004
INVENTOR(S) : Moe et al.

Page 1 of 1

It is certified that error appears in the above-identified patent and that said Letters Patent is hereby corrected as shown below:

Column 24,
Line 41, change "S" to -- 5 --
Line 44, change "halo alkyl" to -- haloalkyl --
Lines 53 and 54, change "halo" and "alkoxy" to -- haloalkoxy --

Column 26,
Line 28, change "tat" to -- that --

Signed and Sealed this

Twenty-fifth Day of May, 2004

JON W. DUDAS
*Acting Director of the United States Patent and Trademark Office*